US009746422B2

(12) United States Patent
Palmieri et al.

(10) Patent No.: US 9,746,422 B2
(45) Date of Patent: Aug. 29, 2017

(54) GEMSTONE REGISTRATION AND RECOVERY SYSTEM, AND SYSTEMS FOR EVALUATING THE LIGHT PERFORMANCE OF A GEMSTONE AND CAPTURING FORENSIC CHARACTERISTICS OF A GEMSTONE

(71) Applicant: Gemological Appraisal Association, Inc., New York, NY (US)

(72) Inventors: Angelo W. Palmieri, New York, NY (US); Donald A. Palmieri, New York, NY (US); Yu Sun, New York, NY (US)

(73) Assignee: GEMOLOGICAL APPRAISAL ASSOCIATION, INC., New York, NY (US)

(*) Notice: Subject to any disclaimer, the term of this patent is extended or adjusted under 35 U.S.C. 154(b) by 39 days.

(21) Appl. No.: 14/723,042

(22) Filed: May 27, 2015

(65) Prior Publication Data

US 2015/0346108 A1    Dec. 3, 2015

Related U.S. Application Data

(60) Provisional application No. 62/003,133, filed on May 27, 2014.

(51) Int. Cl.
| | | |
|---|---|---|
| G01N 21/00 | (2006.01) |
| G01N 21/87 | (2006.01) |
| G01N 21/65 | (2006.01) |
| G01N 21/66 | (2006.01) |
| G01N 21/88 | (2006.01) |

(52) U.S. Cl.
CPC ............ *G01N 21/87* (2013.01); *G01N 21/65* (2013.01); *G01N 21/66* (2013.01); *G01N 21/88* (2013.01)

(58) Field of Classification Search
CPC ...... G01N 21/958; G01N 21/88; G01N 21/87; G01N 21/8806; G01N 21/64; G01N 21/65; G01N 33/38
See application file for complete search history.

(56) References Cited

U.S. PATENT DOCUMENTS

| | | | |
|---|---|---|---|
| 5,036,724 A * | 8/1991 | Rosheim | B25J 9/103 74/490.06 |
| 6,239,867 B1 | 5/2001 | Aggarwal | |
| 2008/0043220 A1* | 2/2008 | Kaplan | B23K 26/032 356/30 |
| 2009/0021036 A1* | 1/2009 | Chang | B60R 11/0235 296/37.8 |
| 2011/0206234 A1 | 8/2011 | Benderly et al. | |
| 2013/0329212 A1 | 12/2013 | High | |

FOREIGN PATENT DOCUMENTS

| | | |
|---|---|---|
| EP | 0 799 110 | 9/1999 |
| WO | WO 2014/058908 | 4/2014 |

* cited by examiner

*Primary Examiner* — Abdullahi Nur
(74) *Attorney, Agent, or Firm* — Leason Ellis LLP

(57) ABSTRACT

A computer-implemented system is provided and includes a processor and a memory accessible by the processor, with the system being configured to measure light performance properties of a gemstone and generate an objective grade for the gemstone.

34 Claims, 13 Drawing Sheets

GEMSTONE REGISTRATION AND RECOVERY SYSTEM, AND SYSTEMS FOR EVALUATING THE LIGHT PERFORMANCE OF A GEMSTONE AND CAPTURING FORENSIC CHARACTERISTICS OF A GEMSTONE

CROSS-REFERENCE TO RELATED APPLICATIONS

The present application claims priority to U.S. patent application Ser. No. 62/003,133, filed May 27, 2014, which is hereby expressly incorporated by reference in its entirety.

The present application is also related to U.S. patent application Ser. No. 14/049,033, filed Oct. 8, 2013, which claims priority to U.S. patent application 61/710,883, filed Oct. 8, 2012, and is also related to U.S. patent application Ser. No. 13/542,100, filed Jul. 5, 2012, and is further related to U.S. Pat. No. 5,124,935; U.S. Pat. No. 5,828,405; and U.S. published patent application No. 2010/0092067, each of which is hereby expressly incorporated by reference in its entirety.

TECHNICAL FIELD

The present invention relates to a system for classifying and recording information with respect to gemstones and providing an owner with an accurate optical identification of the gemstone and provides wholesale and retail establishments, law enforcement, government, and insurance agencies with a verification system and further relates to a system that uses quantifiable and reproducible data to evaluate how well a gemstone is cut by looking at a plurality of different metrics of light performance or light handling ability, including but not limited to light return, brilliance, optical symmetry, scintillation and optionally, light dispersion, etc.

BACKGROUND

Gemstones have their own unique optical response and this optical response can be used for accurate identification of the gemstones. In this regard, U.S. Pat. No. 3,947,120 discloses an arrangement for providing an optical fingerprint of a gemstone where a laser beam is focused on a gemstone and the optical response of the gemstone is recorded on a recording medium, preferably a photographic medium. This arrangement provides a fingerprint of the gemstone which is reproducible and has been held by the courts to be sufficient evidence to prove that the gemstone under consideration having a certain optical response is the same as a previously identified gemstone having essentially the same optical response.

The traditional techniques for evaluating how well a gemstone is cut are very subjective in nature and therefore, subject to different interpretation and also suffer from a lack of complete reproducibility. For example, to properly judge the cut of a diamond, one must know the table diameter (%), the crown angle (in degrees), the pavilion depth (%), the girdle thickness (%), and the culet size, as well as the angles by which they are joined. This sort of information is commonly found for diamonds which have a certification (commonly from GIA, AGS, GCAL, or EGL). Depending upon the cut of the diamond (e.g., round brilliant cut), various laboratories provide different proportions for their top level of cut, which can be "ideal" or "excellent" cut.

As will be appreciated, this type of traditional evaluation of the quality of the gemstone cut is based entirely on the dimensions of the cut and fails to take into account the quality and internal structure of the stone itself. In other words, the ranking of diamond cuts by evaluating the dimensions of the cut assumes a flawless diamond and therefore, most diamonds are not flawless, this traditional system does not take into account the quality and internal structure of the diamond.

SUMMARY

A computer-implemented system is provided and includes a processor and a memory accessible by the processor, with the system being configured to measure light performance properties of a gemstone and generate an objective grade for the gemstone. The system includes a mount in which the gemstone is held and a light source for directing a focused beam of light onto the gemstone to produce an output of the internal refraction and reflection characteristics of the gemstone including reflected light beams having particular locations, sizes and intensities. The system also includes an automated positioning mechanism for changing a position of the gemstone relative to the focused beam of light. The automated positioning mechanism is configured to move a platform on which the gemstone rests according to the following directions: pitch, roll, and yaw rotation.

In addition, a primary imaging device is provided to capture a Gemprint of the gemstone and a secondary imaging device is provided to capture additional image information concerning the gemstone as described herein.

The system includes a client application stored in the memory that, when executed by the processor, configures the system to: (a) measure a light return property, an optical symmetry property and a scintillation property of the gemstone by recording the output in a manner to record the relative size and location of the reflected light beams; and (b) analyze the output with respect to each of the light return property, the optical symmetry property and the scintillation property relative to information stored in a numerical scoring database to generate a grade for each of the light return property, the optical symmetry property and the scintillation property.

These and other aspects, features and advantages shall be apparent from the accompanying Drawings and description of certain embodiments of the invention.

BRIEF DESCRIPTION OF DRAWING FIGURES

DETAILED DESCRIPTION OF CERTAIN EMBODIMENTS

Figure 1:
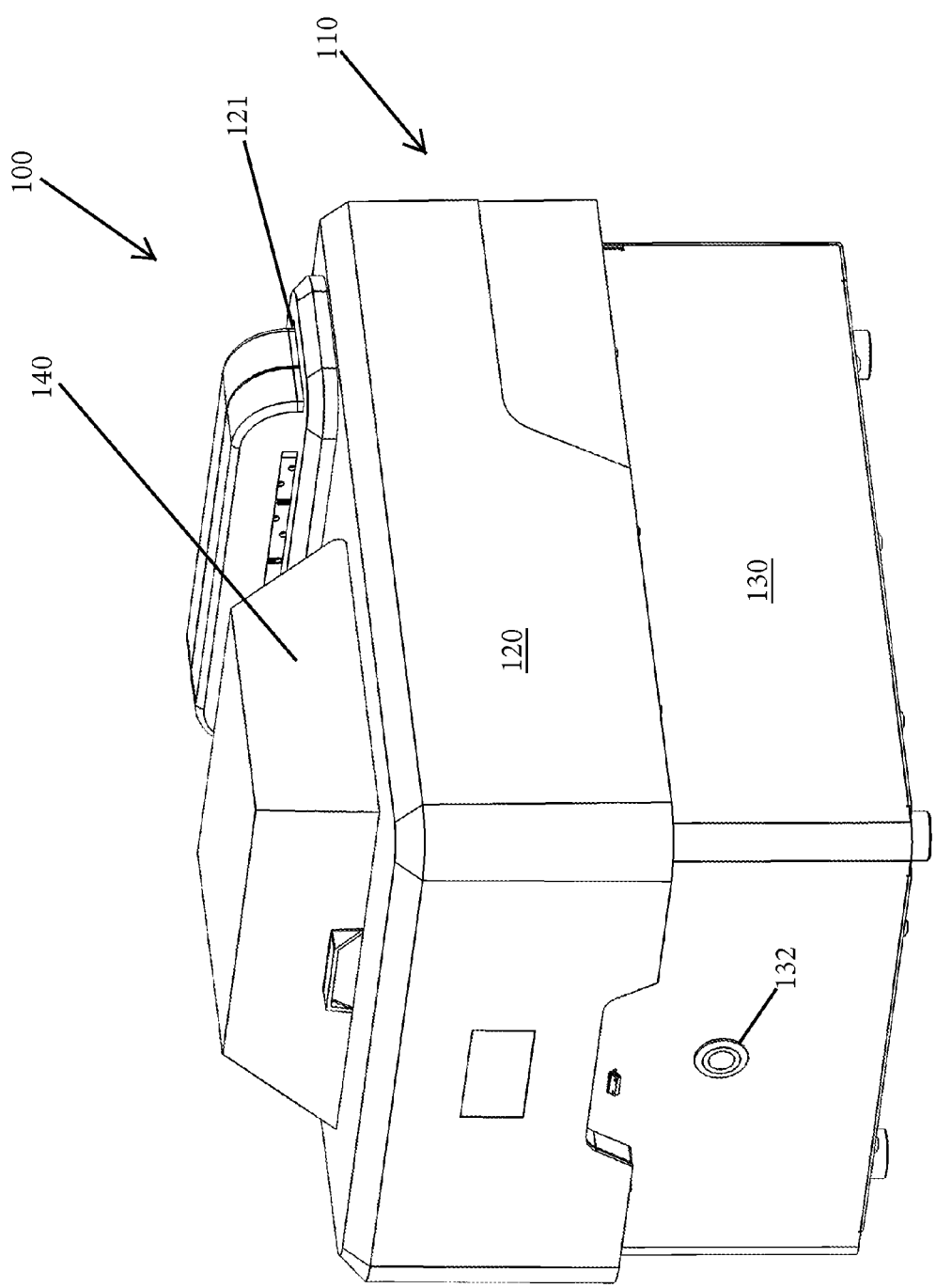
FIG. 1 is front and side perspective view of gem registration device according to one embodiment of the present invention.
Figure 2:
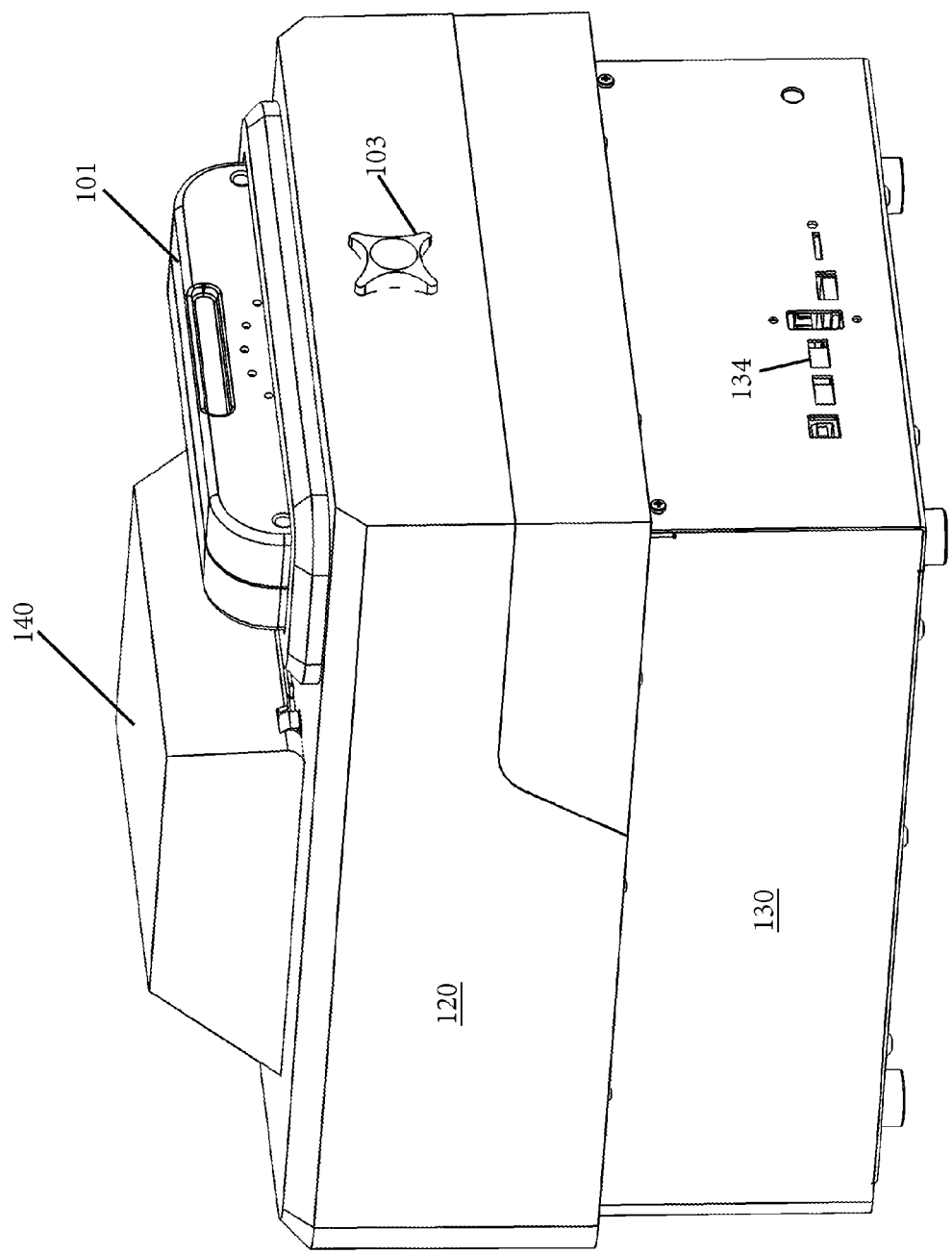
FIG. 2 is rear and side perspective view of the device.
Figure 3:
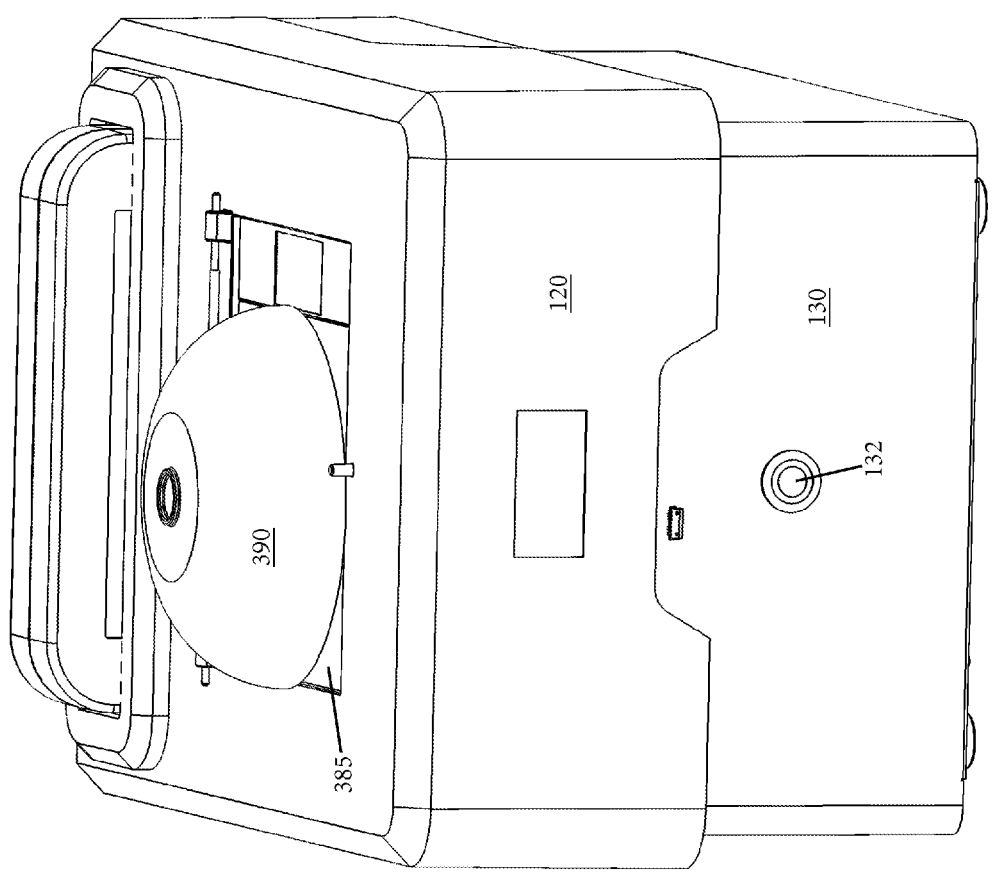
FIG. 3 is a front perspective view thereof.
Figure 4:
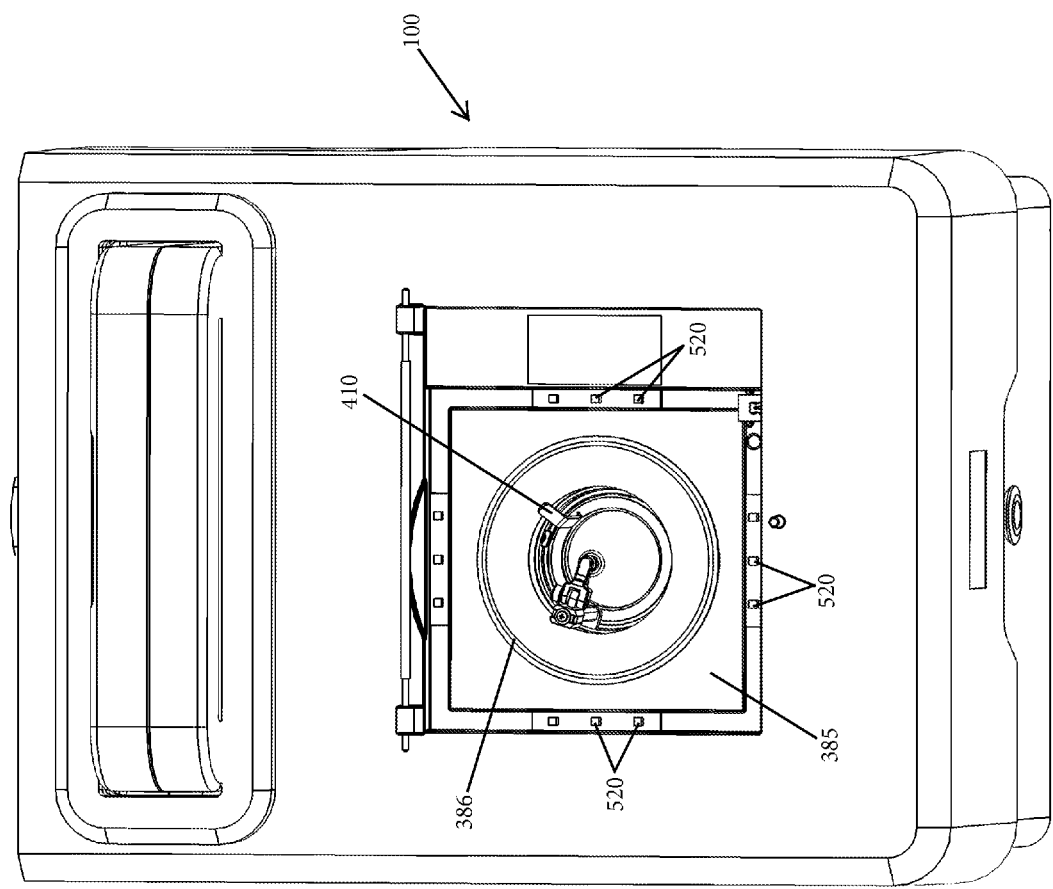
FIG. 4 is a top perspective view thereof with the cover being removed to show additional parts.
Figure 5:
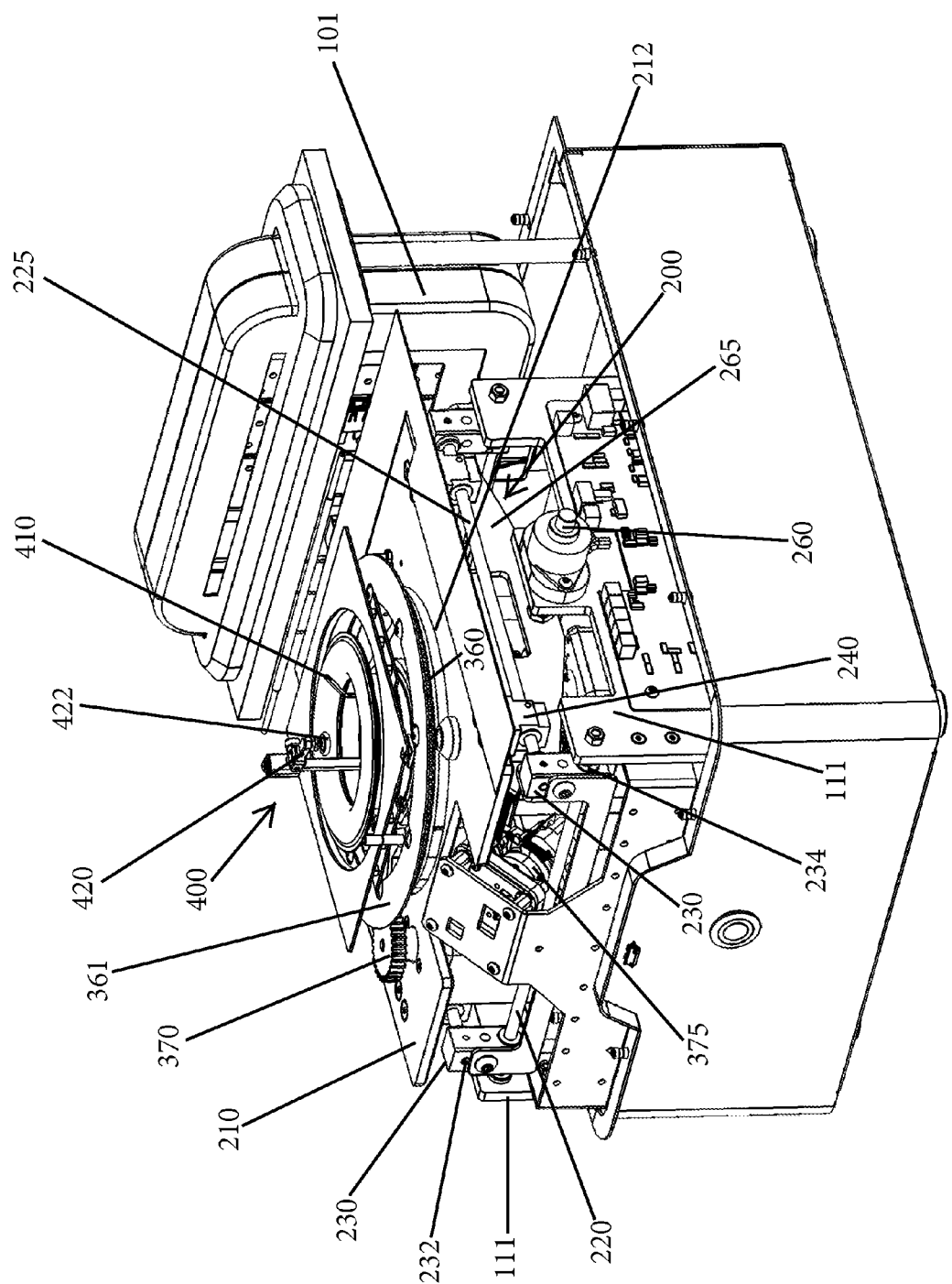
FIG. 5 is a front and side perspective view with a top housing member being removed.
Figure 6:
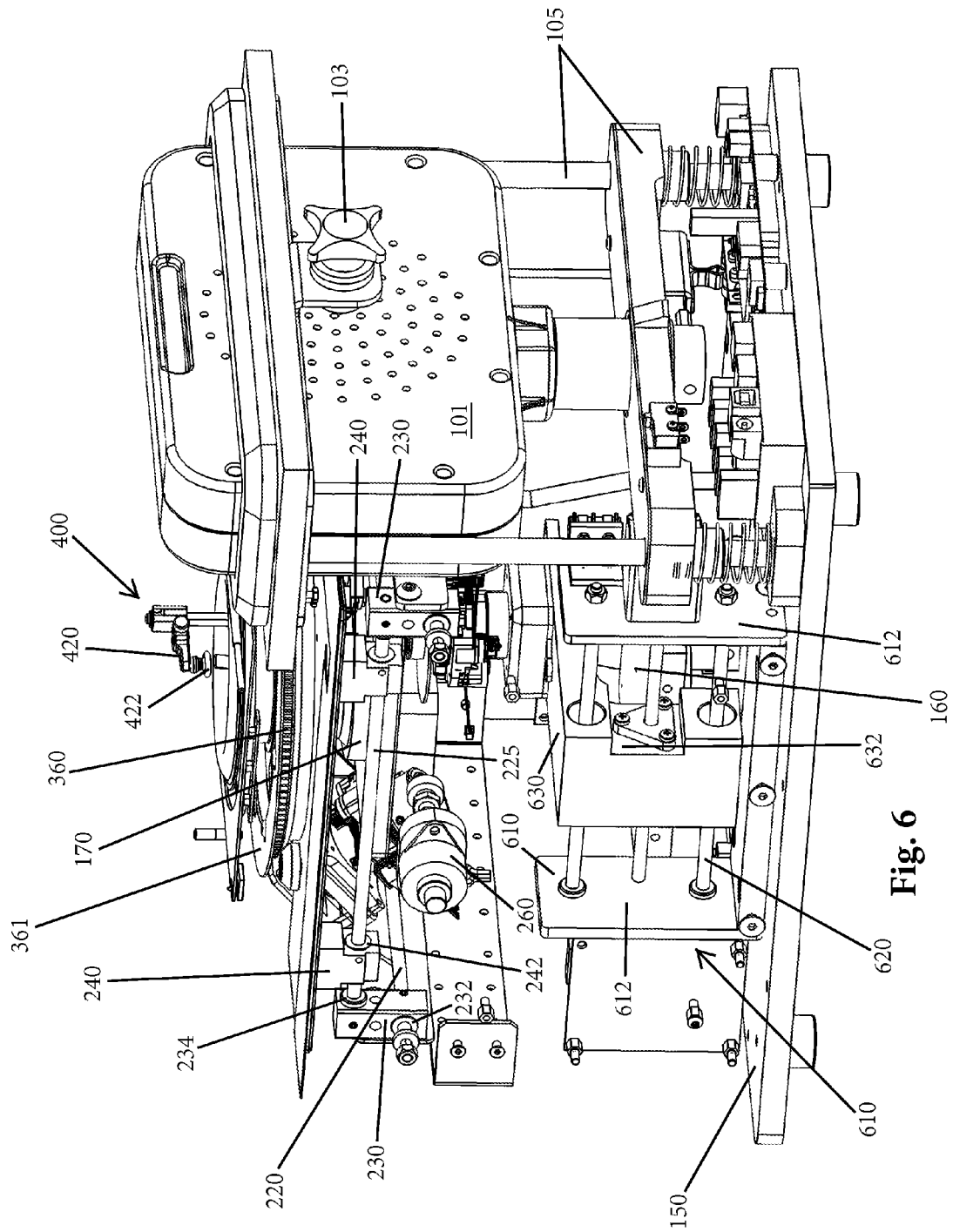
FIG. 6 is rear and side perspective view with the housing being removed.
Figure 7:
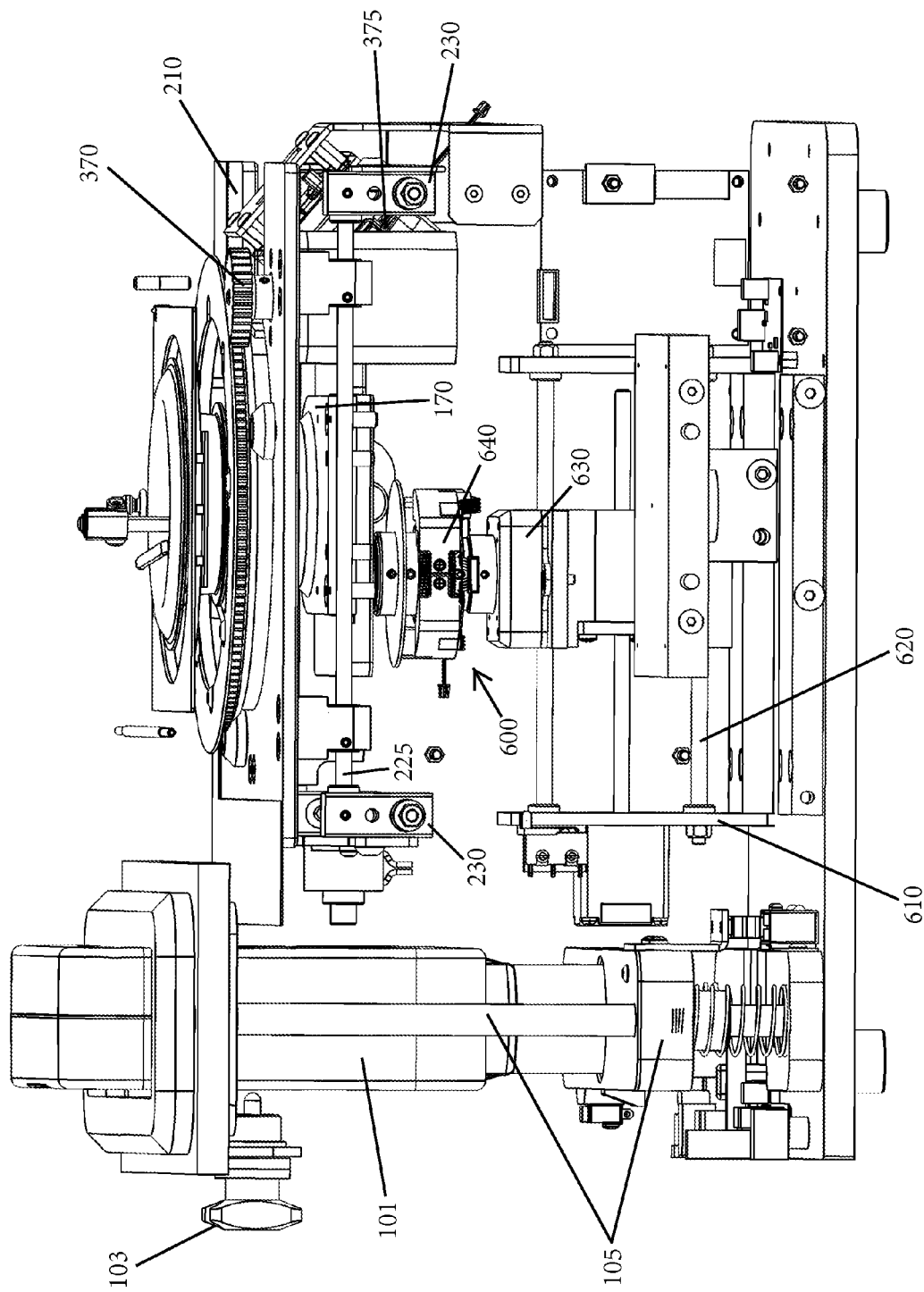
FIG. 7 is a side perspective view with the housing being removed.

FIGS. 1-3 show a gemstone registration device (system) 100 according to one embodiment of the present invention in a fully assembled condition and in particular, the device 100 is in the form of a device for producing an optical pattern by exposing a gemstone to a beam of light. The device 100 is similar to and includes a number of features described with respect to any of the devices disclosed in the patent applications and/or patents incorporated by reference herein, including the device which is described in detail in U.S. patent application publication No. 2014/0063485 (the '485 publication) which is hereby incorporated by reference in its entirety.

As shown in FIGS. 1-12, the device 100 includes a housing 110 that contains the working components of the device 100 and provides a compact, visually pleasing product. The housing 110 is formed of a number of individual parts that are mated together to form the assembled housing 110. More particularly, the housing 110 includes a cover 120 and a base (bottom sidewall portion) 130 to which the cover 120 mates.

The housing 110 is a substantially hollow structure which contains the working components of the device 100. The cover 120 is intended to be secured to the base 130 during normal operation and includes a door member 140 which moves between a closed position (FIG. 1) and an open position which allows insertion and removal of a gemstone. The door member 140 is can be pivotally coupled to the cover 120. The base 130 can include a power button 132 which allows the user to power up the device 100 when actuated by the user. The base 130 can also include one or more ports 134 to allow the device 100 to be connected to an external device such as a personal computer, mobile device, network, etc.

Figure 8:
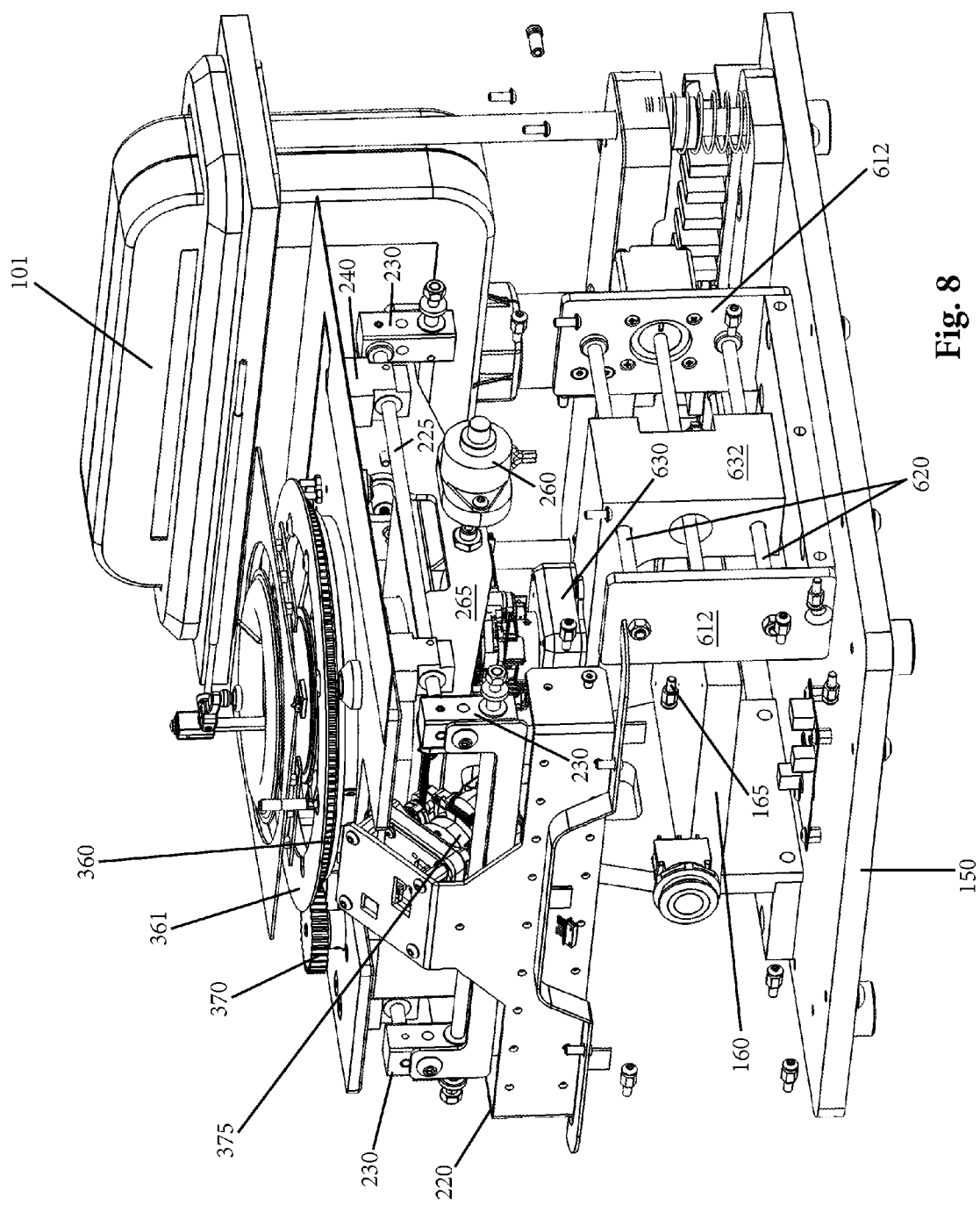
FIG. 8 is a front and side perspective view with the housing being removed.
Figure 9:
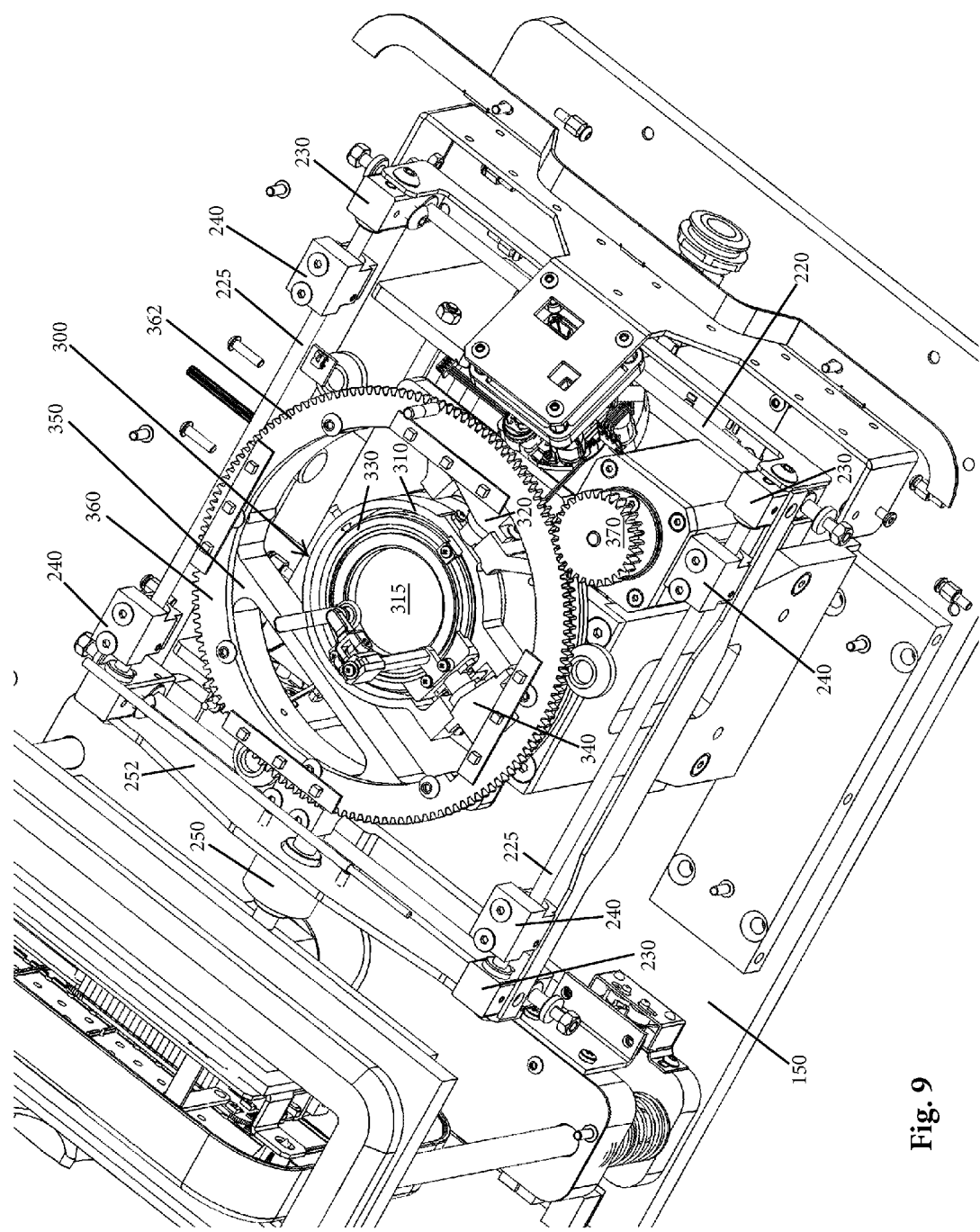
FIG. 9 is a top perspective view of a gimbal assembly.
Figure 10:
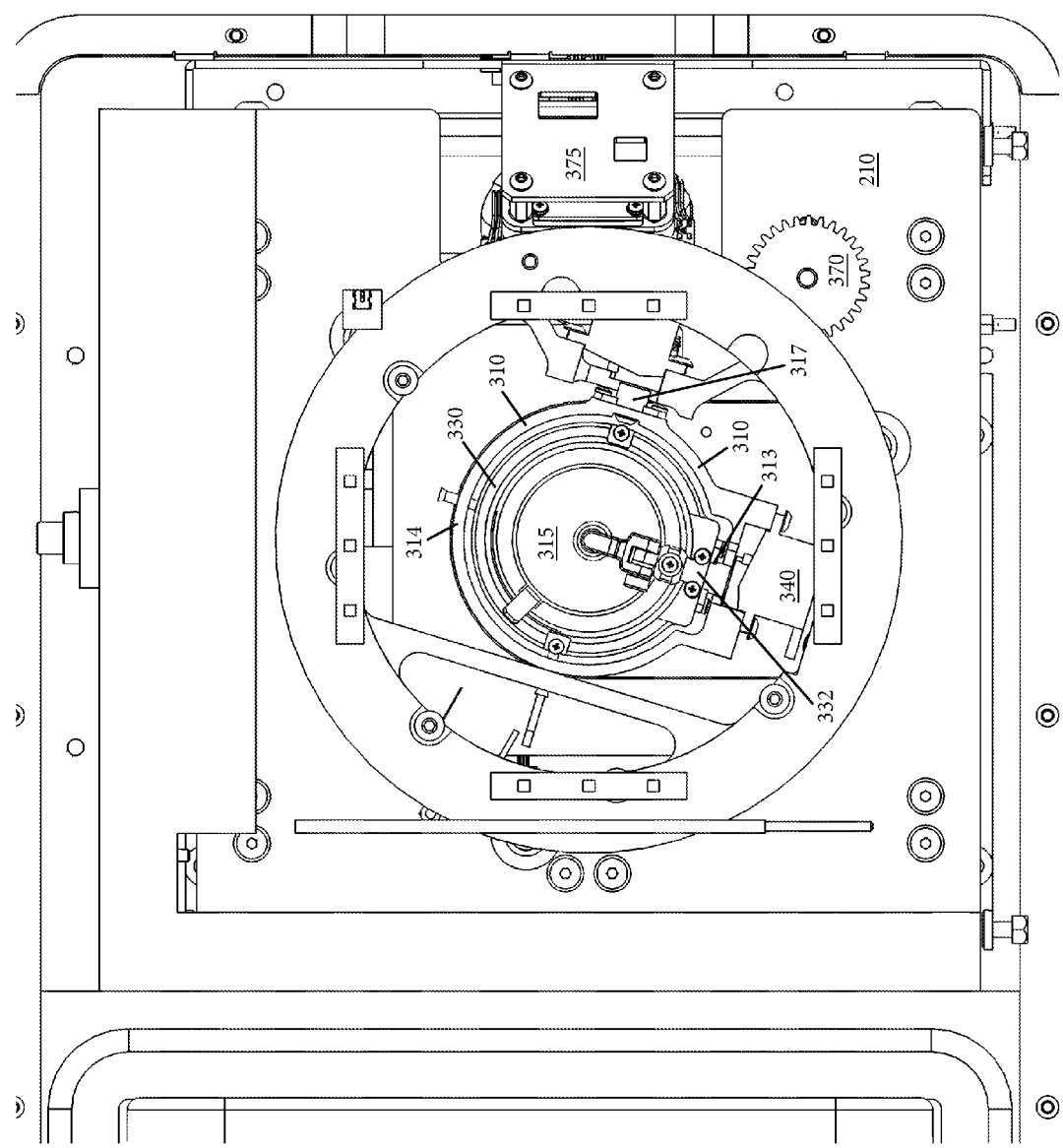
FIG. 10 is a top plan view of the gimbal assembly.
Figure 11:
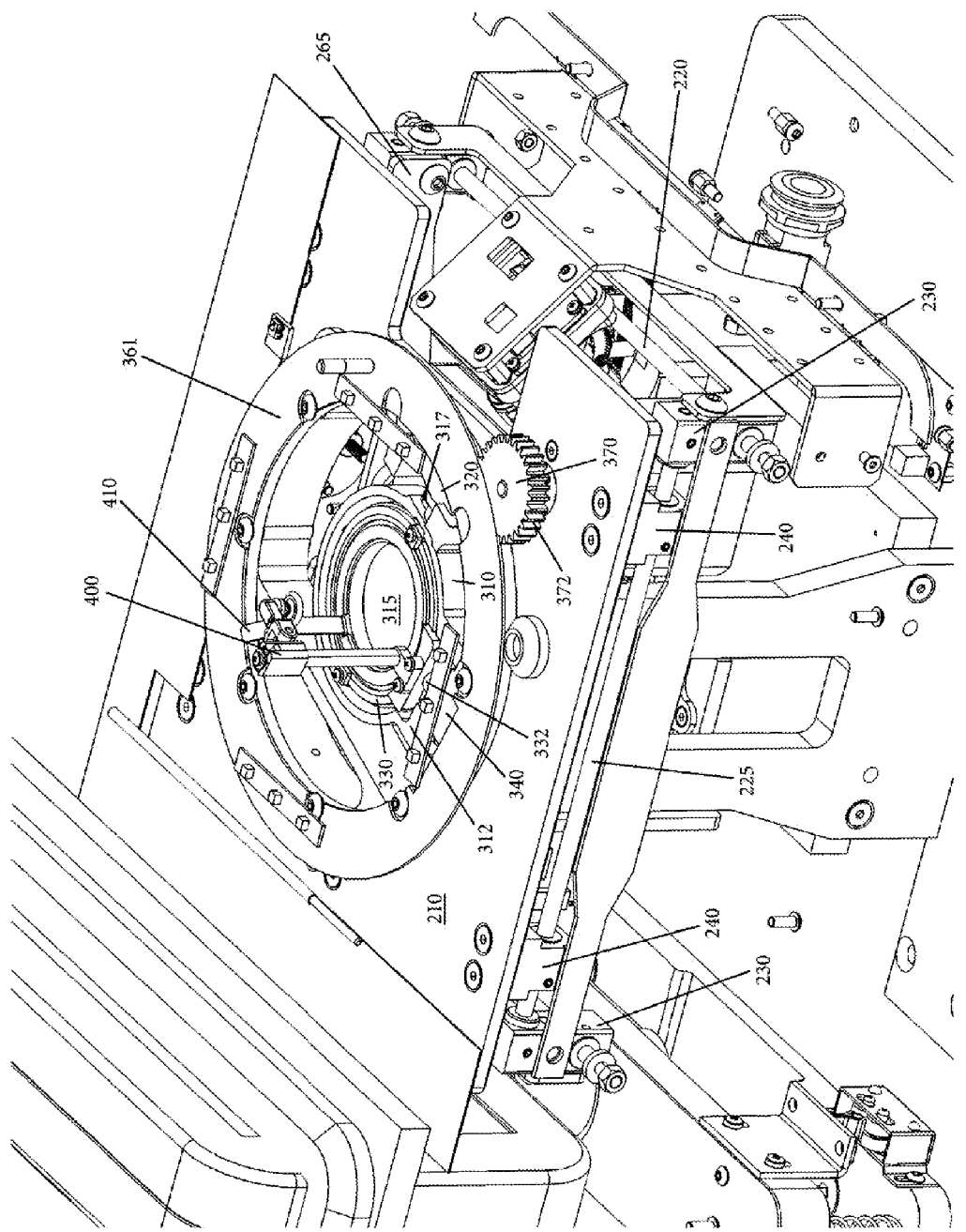
FIG. 11 is a top and side perspective view of the gimbal assembly.

As best shown in FIG. 2, the device 100 can include a display 101, such as an LCD screen or the like (see FIG. 8). The display 101 can be movable between a retracted position (FIG. 1) in which the display 101 is contained within the housing 110 and an extended position in which the display 101 is disposed above the top surface of the housing 110 for easy viewing by the user. A display actuator 103, such as a knob, button, slider, etc., can be manipulated to cause the display 101 to move between the two positions. The display 101 is thus slidably supported on a display frame generally shown at 105. The cover 120 includes an opening/slot 121 through which the display 101 passes. The display 101 can also be configured to freely rotate and/or tilt to allow it to be positioned in an optimal position with respect to an individual user. The actuator 103 can be of a manual type or an automated type and therefore, the display can be manually operated (e.g., cranked) by the user or in an automated version, the user can simply press a button or the like to operate the display 101. The display 101 can be of a touchscreen type that allows direct manipulation by the user.

The display 101 can be a 7" LCD touch screen that has the following features and functions:
1) The addition of the touch screen will allow for all control of the instrument to be handled from the screen. With the addition of a processor internal the instrument, a computer or tablet would no longer be necessary to operate the instrument.
2) The screen is on a spring loaded pole that moves up and down, and allows the user to tuck the screen away after use, or pull the screen up during use and allow the customer to watch everything that is happening in the instrument. The pole also allows for 360 degrees of rotation, so no matter the position of the instrument relative to the customer and user, the screen can be rotated to the proper viewing angle.
3) Finally, the LCD screen will be able to show the customer the live view of the primary camera, secondary camera, or animations sent to the screen through the software application executed by the device.

The device 100 can thus be a standalone unit as shown and can be easily transported.

The housing 110 also includes a bottom base (platform) 150 which completes the housing 110 and is disposed along the bottom thereof and represents a ground contacting portion of the housing. The base 150 is a substantially planar tray-like structure. The base 150 thus includes a bottom wall that represents a floor. The base 150 is a planar surface that seats on a ground surface, such as a table.

When the parts 120, 130 are assembled, the housing 110 only includes one main access point, namely through the door member 140.

The device 100 also includes a number of sub-assemblies that include the working components of the device 100 that ensure proper positioning of the gemstone and generation of a beam of light for producing a unique optical pattern (the gem's "fingerprint") that is generated when the gemstone is exposed to the beam of light as well as images and data collected by the secondary camera. One sub-assembly concerns the optics and light beam generating means.

The device 100 includes a planar substrate 160 that is disposed above the floor of the base 150. The planar substrate 160 is oriented so that is parallel to the floor but spaced therefrom to permit working components to be disposed thereunderneath between the floor and the substrate 160. The planar substrate 160 has a slit or opening 165 formed therein and is generally located in the middle of the substrate 160 and extending from one side to the other side of the generally square shaped substrate 160. This opening 165 allows the focused light beam to exit from its source underneath the substrate 160 and be directed, in a controlled manner, toward the gemstone that rests above the substrate 160 as described herein. In the present embodiment, the light beam is generated centrally relative to the substrate 160 and thus passes through the center of the slit 160. Alternatively, the source of light can be mounted above the substrate 160.

In accordance with the present invention, the light beam generating means is in the form of a laser that is disposed underneath the substrate 160 and aligned with the opening 165 such that the light beam generated by the laser passes through the opening 165 in an unimpeded manner.

The laser is operatively connected to a power source and a controller, such as a printed circuit board (PCB) to allow the controlled operation of the laser.

As discussed herein, the device 100 is an electronic device and therefore includes a processor and other electronics to control operation of the various components and to allow processing of data collected by the components of the device 100. Further, the device 100 can be connected to a peripheral device, such as a computer (personal computer) to allow the data collected by the device 100 to be stored (in memory) and processed by the computer which contains a processor that executes code (software) to allow precise control of the gemstone positioning and to allow imaging to be displayed (live video feed) as discussed herein.

Any number of suitable lasers can be used so long as they perform the intended function, including a solid state laser diode. The laser cooperates with an optical arrangement to produce a collimated focused laser light beam. The optical arrangement adapts this type of laser to the required, focused, precise light beam suitable to this application. The light beam passes through a narrow opening formed in the substrate 160 which, as described herein, functions as a screen.

As described below, the collimated beam passes through another optical arrangement and subsequently strikes the gemstone that is supported and oriented such that the table of the gemstone is perpendicular to the light beam. The optical arrangement includes a lens assembly that acts on the light beam.

Each gemstone, due to the inherent properties of the gemstone and the cutting of the gemstone, produces a unique optical response which can be distinguished from the optical response from other gemstones. As each gemstone is aligned and centered relative to the beam as described herein, the optical response is inherent to the gemstone such that the optical pattern is consistent. This optical pattern, however, will be at a different rotational position relative to the axis of the light beam as the gemstone position changes and based on the initial placement and orientation of the gemstone.

In order to mount the optical arrangement, an optics mount assembly 170 is provided and includes a lens. Additional details concerning an exemplary optics mount assembly 170, including the lens, are set forth in the '485 publication.

In accordance with the present invention, an imaging/recording device 375 is provided for capturing the optical output response that is unique to the gemstone. According to one embodiment, the device 375 is in the form of a charge couple device, such as a two-dimensional CCD (charge couple device) video camera 375 is positioned and is directed at the screen (substrate) 160. The two-dimensional CCD camera 375 is adjusted to cover the focused optical response provided on the screen, allowing this entire image to be captured at the same point in time. Additional details concerning the camera 375 are set forth in the '485 publication. The camera 375 can be thought of as being a primary camera that is used to collect data used to create (calculate) the gemprint.

As discussed in Applicant's prior patents, a calibration system can be provided for calibrating the camera position relative to the substrate 160.

The device 100 also includes a gemstone holder assembly 200 (FIG. 5) that is adjustable to allow the position of the gemstone to be adjusted relative to the light beam in order to allow optimal alignment of the gemstone to be achieved. As discussed herein, the assembly 200 is an automated mechanism that allows the gemstone to be adjusted in more than two directions.

The gemstone holder assembly 200 includes a motion plate 210 that includes a central opening 212 which is disposed above the light beam such that the motion plate 210 does not interfere with the passage of the light beam. The motion plate 210 supports a gimbal assembly 300 (FIG. 9) as described herein. The motion plate 210 can be controllably moved in two directions, namely, an X direction and a Y direction. The housing 110 includes a pair of side walls 111 and a pair of first guide rods 220 is disposed between the two side walls 111. One first guide rod 220 is located at the front, while the other first guide rod 220 is located at the rear. The spaced guide rods 220 can be attached at their ends to the two respective side walls 111.

The assembly 200 includes a plurality of two-way slide supports 230 that represent block-like structures that have through holes formed therein. In the illustrated embodiment, there are four two-way supports 230 located in the four corners of the plate 210 which has a square shape. Each support 230 includes a first passage or through hole (bore) 232 and a second passage or through hole (bore) 234 which is formed perpendicular to the first through hole 232. The first passage 232 is located above the second passage 234 when the support 230 is oriented in its normal operating position. The first guide rod 220 is disposed within the second passage 234 in a sliding manner in that each support 230 can slide along the first guide rod 220.

The supports 230 thus represent a support frame on which the motion plate 210 is supported. The two guide rods 220 are located parallel to one another and therefore can be thought of as extending in the x direction. As such, when the supports 230 move along the respective rods 220, the plate 210 moves in the x direction a predetermined distance as described herein.

The assembly also includes a pair of second guide rods 225 that are disposed in a plane above the plane that contains the first guide rods 220. The second guide rods 225 are oriented parallel to one another and along axes that are perpendicular to axes that contain the first guide rods 220. Each second guide rod 225 is disposed between two supports 230 and the ends of the second guide rod 225 pass through the first passage 232 of the respective supports 230.

A plurality of one-way slide supports 240 is provided along each of the second guide rods 225. Each one-way slide support 240 is coupled to the underside of the motion plate 210 and includes a through hole 242 through which the second guide rod 225 passes, thereby allowing the one-way slide supports 240 to slide along the second guide rod 225. Since the one-way supports 240 are coupled to the underside of the motion plate 210, the plate 210 can move a predetermined distance along the second guide rods 225 in the y direction.

It will therefore be appreciated that the first and second guide rods 220, 225 in combination with the supports 230, 240 allow the motion plate 210 to move a controlled distance in both the x and y directions. This allows for the gemstone supported on the motion plate 210 as described herein to be moved to a target location relative to the laser source at least in the x, y directions.

The movement of the motion plate 210 is controlled by one or more actuators and in particular, a first linear actuator (stepper motor) 250 can be provided and is coupled to the motion plate 210. The first motor 250 is configured to drive the motion plate 210 in the y-direction along the second rails 225. The first motor 250 (linear actuator) can be coupled to the motion plate 210 by a drive plate 252 (Y-direction) that is attached to the motion plate 210. As a result, the controlled operation of the first motor 250 causes controlled incremental movement of the motion plate 210 in the Y-direction. Similarly, a second linear actuator (stepper motor) 260 can be provided and be coupled to the motion plate 210 to cause controlled movement thereof in the X-direction. For example, a drive plate 265 can be coupled at its ends to two two-way slide supports 230. Thus, linear driving of the drive plate 265 in the x-direction is translated to the two-way slide supports 230 being driven in the x-direction and this in turn causes the motion plate 210 to move in the x-direction.

As a result, the controlled operation of the two linear actuators 250, 260 allows for controlled, precise movement of the motion plate 210 in each of the x and y directions.

The gemstone holder assembly also includes the gimbal assembly 300 which is mounted and carried by the motion plate 210. As is known, a gimbal is a pivoted support that allows the rotation of an object about a single axis. A set of two gimbals, one mounted on the other with pivot axes orthogonal, may be used to allow an object mounted on the innermost gimbal to remain immobile (i.e., vertical in the animation) regardless of the motion of its support. The gimbal assembly 300 is in the form of a double gimbal (as in the device disclosed in the '485 publication) and more specifically, the gimbal assembly 300 includes a first gimbal 310 that represents an outer gimbal. The first gimbal 310 is a continuous structure that has a flat back wall 312 and a rounded front wall 314 and thus is generally in the form of a ring. The first gimbal 310 is a hollow member in that a central opening is formed therein. Along the back wall 312, a notch 313 is formed (e.g., a U-shaped notch). In addition, along one side of the first gimbal 310, a first coupling member 317 is mounted to one side and protrudes outwardly therefrom. In the illustrated embodiment, the first coupling member 317 is a hollow arm structure that is coupled to a drive shaft of a first gimbal motor 320 for controlled movement of the first gimbal 310.

The first gimbal 310 is thus supported and operatively connected to the first gimbal motor 320 that imparts movement to the first gimbal 310. For example, the motor 320 can be a servo motor that provides precise control over the movement of the first gimbal 310. Under the driving action of the first gimbal motor 310, the first gimbal 310 rotates about a first axis. Since the first gimbal 310 and the related parts, such as motor 320, are carried by the motion plate 210, these parts likewise move in the x and y directions with the motion plate 210.

The gimbal assembly 300 also includes a second gimbal 330 that represents an inner gimbal. The second gimbal 330 is configured to rest within the hollow interior space of the first gimbal 310. The second gimbal 330 is generally circular in shape and is continuous and thus represents an inner ring. The second gimbal 330 includes a coupling member 332 that is attached to a rear section of the second gimbal 330. The coupling member 332 can be a separate member that is attached to the rear section of the second gimbal 330. The coupling member 332 is configured to mate and couple the second gimbal 330 to a device 340 that imparts movement to the second gimbal 330. For example, the device 340 can be in the form of a second gimbal motor, such as a servo motor, that provides precise control over the movement of the second gimbal 330. The coupling member 332 can include a hollow arm structure that receives a drive shaft that is operatively connected to the second gimbal motor 340. The operation of the second gimbal motor 340 imparts pivoting movement to the second gimbal 330.

As with the first gimbal 310, the second gimbal 330 is supported and carried by the motion plate 210.

The inner second gimbal 330 freely pivots along a second axis that extends through the drive shaft of motor 340. As mentioned above, the first and second pivot axes are orthogonal to one another as is custom in a double gimbal design.

The inner second gimbal 310 supports and holds a transparent plate 315 that in turn receives and supports the gemstone on an outer facing surface thereof. The transparent plate 315 can be a glass disk as shown. The center of the transparent plate 315 is axially aligned with the laser resulting in the light beam being centrally focused relative to the transparent plate 315. The gemstone is disposed on the transparent plate 315 in a table down orientation. To ensure proper operation, the gemstone should be disposed initially in a central location of the transparent plate 315.

The motion of the first and second gimbals thus allows the gemstone on plate 315 to be moved in pitch and roll motions.

In accordance with the present invention, the gimbal assembly 300 has another degree of motion and in particular, gimbal assembly has yaw motion. As is known, a yaw rotation is a movement around a yaw axis.

A yaw frame 350 (FIG. 9) which is circular in nature serves as a support to which the first and second gimbals are mounted such that rotation of the yaw frame 350 results in rotation of the gimbals and the plate 315 supported thereby. The yaw frame 350 is substantially hollow and the first and second gimbals are disposed within the hollow center. A yaw (spur) gear 360 is coupled to the yaw frame 350 and surrounds the first and second gimbals. The yaw gear 360 is thus an annular shaped gear that has a hollow center in which the two gimbals are disposed. An outer surface of the yaw gear 360 includes teeth 362. The yaw frame 350 is thus disposed at least partially within the opening formed in the motion plate 210 and the yaw gear 360 surrounds this opening and is disposed above the top surface of the motion plate 210.

A top cover plate 361 can be disposed above the yaw gear 360 for covering the yaw gear 360.

The yaw gear 360 is driven by a drive (pinion) gear 370 which is operatively coupled to an actuator, such as a stepper motor 380, and includes teeth 372. Like the yaw gear 360, the drive gear 370 is disposed along the top surface of the motion plate 210 and mates with the yaw gear 360 (i.e., teeth 372 mate with teeth 362).

The motion plate 210 further includes a hole through which a drive shaft passes to connect the drive gear 370 to the motor 380 which is disposed below the motion plate 210. Operation of the motor 380 thus causes rotation of the drive shaft and rotation of the drive gear 370 which is translated into rotation of the yaw gear 360. This motion is directly translated into rotation of the first and second gimbals and rotation of the plate 315 on which the gemstone is situated. The stepper motor 380 allows for precision movement of the first and second gimbals in the yaw direction (yaw rotation).

The gimbal assembly 300 thus has three distinct degrees of motion, namely, pitch, roll and yaw. This degree of motion allows for optimal positioning of the gemstone relative to the laser. All three motions are controlled with precision using the user interface disclosed herein.

The device 100 also further includes a gemstone centering mechanism 400 which can be any number of different mechanisms including those described in the applications incorporated by reference herein.

In the illustrated embodiment, the centering mechanism 400 can be a manual mechanism. In the illustrated embodiment, the centering mechanism 400 has an iris diaphragm construction and in particular, the mechanism 400 is a shutter mechanism (similar to a camera) that is in the form of a circular device with a variable diameter. The mechanism 400 utilizes a diaphragm with a top aligned disc and a lever that allows the user to control the diaphragm from above. In particular, the mechanism includes a circular body that has a hollow center. The diaphragm collapses on the body of the gemstone (jewelry (e.g. set ring) from all directions and physically centers the object on the plate 315.

Along the circular body, a tab (lever) 410 is provided. The tab 410 is an upstanding member relative to the circular body that provides a thumb grasp for a user to allow the user to adjust the shutter. The tab 410 is thus part of the shutter actuator and can move toward and away from the center of the circular body (defined within the hollow center of the body). Thus, the user can place a thumb on the tab 410 and slide it linearly toward the center of the body so as to collapse blade elements that are located within the center opening of the body. The blade elements define a center opening (iris) that has a variable diameter depending upon the precise location of the blade elements. For example, if the user pushes the tab 410 toward the innermost location, the blade elements expand and define a center opening of minimum diameter. Conversely, when the tab 410 is pulled radially outward to the body, the blades collapse and define a center opening of maximum diameter.

The mechanism 400 is constructed to apply a centering force to a gemstone that is seated on the transparent plate 315 to provide an initial rough alignment. This centering force corrects some misalignment of the gemstone on the transparent plate 315 and ensures that the gemstone is placed directly in the center of the plate 315 and is thus axially aligned with the light beam of the laser. This centering ensures that the optical pattern is properly generated and recorded due to the optimal positioning of the gemstone on the plate 315 (plastic or glass plate).

A gemstone retainer member 420 is provided and includes an upstanding arm that is pivotable (rotatable) and includes a plunger 422 or the like at its end for contacting the stone on the plate 315. In one embodiment, shown in FIG. 13, the member 420 can be a spring load member that can ride vertically along a vertical post and locked in a desired place (the member 420 likewise rotates about the vertical post). The spring loaded member 420 operates by pressing in spring-loaded actuator of the member 420 to allow the member 420 to be moved vertically along the post. Once a desired vertical position is reached, the actuator is released causing the member 420 to be locked in a vertical position using a traditional locking mechanism.

In accordance with the present invention, the device 100 includes a light system 500 and a secondary imaging assembly 600. The light system 500 is designed to provide light within the device 100 at desired location and in particular, to bath the gemstone in light from different locations, etc. As described herein, the light system 500 is designed at least in part to work in combination with the secondary imaging assembly 600 to provide an image, video, etc., of the gemstone (the primary light source (laser) is not active during this imaging).

In one embodiment, the light system 500 includes a first light source 510 that is located below the gemstone (i.e., below the plate 315) and a second light source 520 that is located above the gemstone. The first light source 510 can be in the form of one or more lights that are configured and disposed within the interior of the housing 110 such that when the lights are operated, the first light source illuminates the gemstone on plate 315 from the underside.

In one embodiment, the first light source 510 includes a plurality of lights that are fixedly mounted within the housing 110. The lights 510 can be of the type that can be individually positioned within the housing 110 and more particularly, can be of the type (e.g., a canister light) that pivots to allow the lights 510 to be adjusted to customize the illumination within the housing 110.

The lights 510 can be lights that have individual housings that are mounted within the housing, such as being mounted along the first guide rods 220, it will be appreciated that the first light source 510 can be any number of other types of light arrangements. For example, the first light source 510 can be part of or coupled to the lens mount 170 which holds the lens beneath the plate 315 on which the gemstone rests. The lights 510 can thus be located in a circular pattern about the center opening of the mount so as to not interfere with the passage of the laser beam through the mounted lens and the overlying plate 315 on which the gemstone rests. In this embodiment, the lights 510 can be upwardly directed lights that serve to illuminate the underside of the plate 315 and thus, provide illumination of the gemstone.

Figure 12:
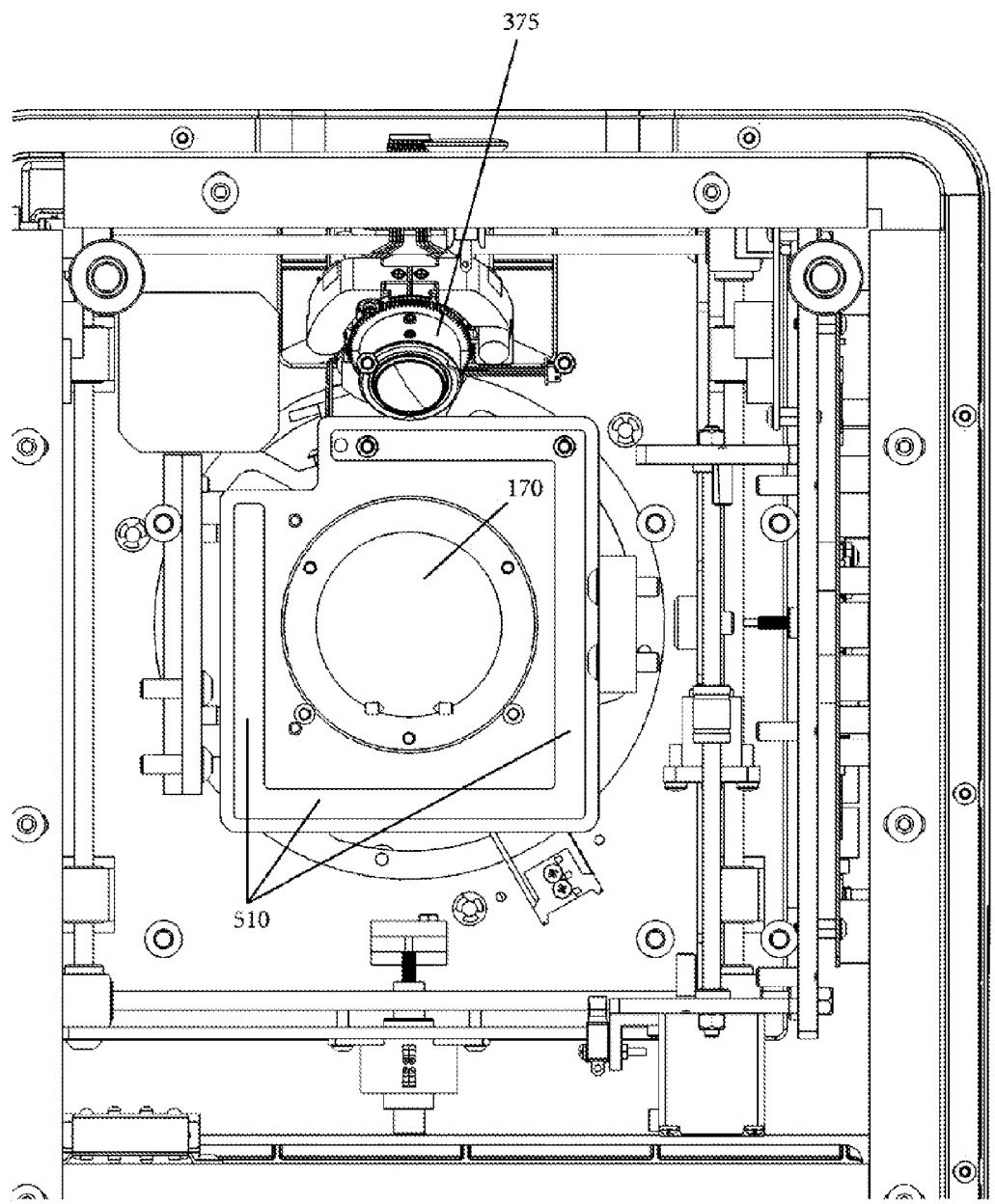
FIG. 12 is a top plan view of the device within the bottom housing removed to show a lighting system in the device.

FIG. 12 is a bottom plan view with the bottom of the housing 110 removed to show the first lights 510 which in this embodiment are in the form of a band (ring) of lights that are formed around the lens and serve to illuminate the plate 315 and thus, the gemstone itself. The first lights 510 take essentially a square shape that has one corner missing (see the notch in the lens mount in the figure). The primary camera 375 is shown in FIG. 12 as well.

As mentioned, the second light source is disposed above the first light source to illuminate the plate 315 and the gemstone sitting thereon in a different manner compared to the first light source.

Figure 13:
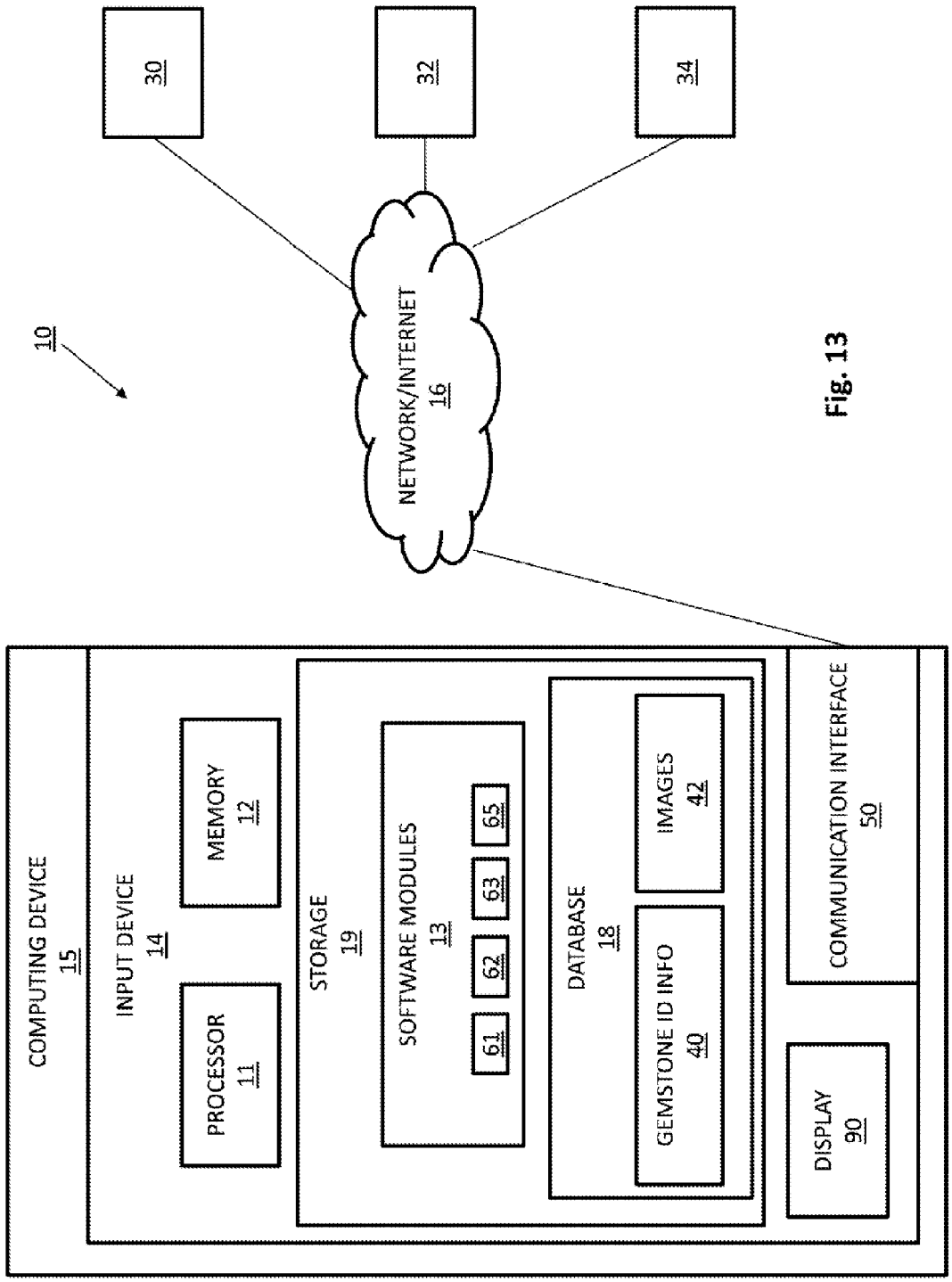
FIG. 13 is a block diagram of components of an exemplary computer system.

The second light source 520 can be located in a base plate 385 that surrounds and is disposed above the plate 315 on which the gemstone sits as shown in FIG. 13. The plate 385 can be part of cover 120 and includes a center opening 386. The lights 520 can be disposed in multiple discrete locations about the opening 386 (e.g., four light segments as shown).

In this location, the lights can be directed such that they illuminate light upwardly. An underside of the door member 140 can include a dome-shaped structure 390 (FIG. 13) that is disposed over the gemstone when the door member 140 is shut. The second light source 520 can be configured such that light is directed upward toward the dome-shaped structure 390 to cause illumination of the area around the top surface of the plate 315. When the door member 140 is shut, the dome-shaped structure 390 seats against the top of the plate 385 and thus operation of lights 520 can illuminate the area between the dome-shaped structure 390 and the plate 315 on which the gemstone sits.

It will be appreciated that the two different light sources allow the user to detect different light properties and perform different analysis on the gemstone and further allows different types of imaging to be performed. The different light sources can be controlled independently to allow the user to turn on one light source (e.g., the first light source or the second light source) or turn on both (all) light sources.

As discussed herein, additional lighting systems that have been added to facilitate additional analysis, measurements, and points of identification. In at least one embodiment:

1) Energy efficient LED's—LED lights have been placed in strategic positions throughout the system to provide effective lighting for various analysis, photography, and photomicrography. All LED's are controlled separately through software for on/off/intensity.
2) UV lights—longwave UV and shortwave UV lights have been placed in the system to capture and record the gemstones reaction to various forms of light. These lights are controlled separately through software for on/off/intensity. In one embodiment, the lights can be below the platform 315 or above the platform 315 to illuminate the gemstone and allow the secondary camera 600 to take an image (photo) of the gemstone (in its excited state for purposes of gemstone identification, such as 3) White lights—added to the secondary camera stage for direct assessment of scintillation and dispersion measurements.

It will therefore be understood that one or more of light sources 510, 520 can be any of the above types of lights.

The secondary imaging assembly 600 supplements the primary imaging device 375; however, as described herein, the secondary imaging assembly 600 can be used for different purposes.

In accordance with the present invention, the secondary imaging assembly 600 can be adjustable in that it is configured to move between at least two positions. More specifically, the secondary imaging assembly 600 moves between a first position in which the device is in a home position and a second position in which the device is in an imaging position (FIG. 8). In the home position, the secondary imaging assembly 600 is offset and remote from the laser beam axis to permit the laser beam to strike the gemstone resting on plate 215.

The secondary imaging assembly 600 can be disposed and mounted to the base 150. In the illustrated embodiment, the substrate 160 is supported on a frame 610 which is mounted to the base 150. The substrate 160 is supported on the frame 610 in such a manner that the substrate 160 is elevated (spaced) from the base 150. The substrate 160 and base 150 can be parallel to one another as shown. The frame 610 further includes end supports 612 and a pair of guide rails 620 that are secured to and extend between the end supports 612. The second imaging assembly 600 includes a movable platform 630 which rides along the guide rails 620. More particularly, the platform 630 has a plurality of supports 632 which each has a through hole that receives one guide rail 620 to permit the support 632 to slidingly travel along the one guide rail 620. The supports 632 are coupled to an underside of the platform 630 and thus, both the supports 632 and the platform 630 move linearly along the guide rails 620.

As shown in the figures, the support 632 can be an L-shaped structure that slidingly travels along a plurality of guide rails 620 with the platform 630 being a top surface of the support 632.

In accordance with the present invention, the secondary imaging assembly 600 includes an imaging device 640 for capturing an image of the gemstone. The imaging device 640 can be any number of different types of camera devices that are suitable for the intended application and are configured to either capture an image and/or video of the gemstone. These images can be displayed on display 101 and/or stored in memory and/or set to another device over a network, etc.

An actuator is used to controllably drive the movable platform 630 and camera 640 which is carried thereby along the guide rails 620 to move the camera 640 between the home position and the in-use imaging position. For example, the actuator can be a linear actuator, such as a stepper motor, which drives the platform 630.

In the previous versions of the Gemprint instrument as illustrated in the '485 publication, only one camera was used to capture the Gemprint reflection patterns. In the present invention, a second hi-resolution camera 640 has been added to the device 100. The secondary camera 640, unlike the primary camera 375, faces in an upward direction from the bottom of the device 100 looking up at the gemstone. As discussed herein, because the placement of the secondary camera 640 would obstruct the laser reflection pattern of the diamond to the image plate, the secondary camera's home position is offset from the center of the instrument, and is brought to the center by motorized controls. The camera 640 comes directly underneath the achromatic lens (lens mount 170) to image the gemstone, and is then moved back to its home position by motor control after the images have been taken.

The secondary camera 640 performs a number of functions including but not limited to:

1) Photography—the secondary camera takes an image of the gemstone or gemstone jewelry placed in the instrument (on the platform 315). The first photograph taken is of the entire object and provides an additional point of identification. The photo is stored in memory as described herein and is associated with the gemstone being investigated.
2) Inclusion Photography—because the camera is high resolution (HD), its placement being controlled by motors, and the stage (platform 315) that holds the gemstone being able to move in pitch, roll, x, y, and z motion, the user can manipulate the gemstone in all directions, planes, and angles, to direct the camera in the right position to capture the inclusions contained in the gemstone. This is another important point of identification of the gemstone.
3) Shape Detection—the secondary camera is able to take a photograph of the gemstone, and using many parameters, including edge detection, the system is able to determine the shape of the gemstone being Gemprinted (being imaged).
4) Measurements—Adding to the shape detection, the photograph will allow one to measure the length and width or minimum and maximum diameter of the stone.
5) Weight Estimation—in combination with the shape detection, and measurement analysis, and average depth % for individual shapes, the user is able to approximate the weight of the gemstone. Additionally, to refine the depth estimate, we will use our light return analysis to gauge how deep or how shallow the gemstone is.
6) Damage Detection—further to the above, photographing the object will allow for damage, chips, nicks, scratches, etc. to be identified and included as points of identification.
7) Ultraviolet Characteristics—as will be discussed below, with the addition of long and short wave ultraviolet lights, the present system is able to capture, photograph, and measure the gemstones reaction to the LW and SW UV lights—for further point of identification. The UV light excites the gemstone and the secondary camera can take a photo of the excited stone for identification purposes (e.g., to see if the gemstone is a synthetic stone, etc.).
8) Light Return/Optical Symmetry, Scintillation, Dispersion—the present device 100 is able to capture both the output of the laser/white light reflections, but also, the direct assessment image of the gemstone when exposed to varying light conditions, backgrounds, and electro-optical settings.

While the primary imaging device 375 is shown as being fixed, it will be appreciated that the primary imaging device 375 can be configured such that it moves between different positions to allow for optimal collection of gemprint light refractions.

As described herein and in the '485 publication, the Gemprint device 100 is an identification system for diamonds that records the unique and subtle distinctions in diamonds, just as fingerprinting does for people. Completely noninvasive, Gemprint technology works by shining a low-powered laser light at a diamond, which is refracted within the diamond and reflected from every facet and internal characteristic. The light coming back from the diamond is a distinct 'optical fingerprint'—a Gemprint—that is recorded and saved in a database shared instantly among a global network of jewelers, law-enforcement and government officials.

In addition, other changes relative to the device disclosed in the '485 publication include but are not limited to the following:

Larger Stage

The stage/coated glass/achromatic lens have been increased by 100% to allow for larger gemstones/jewelry to be Gemprint and analyzed.

Unique Centering/Holding Device

Through its unique design, the jewelry arm can center the diaphragm, and the new centering device is controlled by springs for tension, by parallel bars to keep it from rotating when in use, but the parallel bars end ⅞ the length of the jewelry arm so it can be rotated out of the space when not needed.

Automated Electronics/Camera Controllers

In the device 100, all cameras, lenses, motors, lights, and functionality to be controlled through software.

Additional Motor Movements for Full Spectrum Analysis

Additional motors have been added to provide a full spectrum analysis of the gemstone so that every angle, direction, plane, horizontal, or vertical position can be adjusted. All cameras/lenses and lights are controlled by motors as well for optimal positioning. The instrument has pitch, roll, yaw, horizontal, and vertical position for each gemstone as described herein.

Computer System

As in the device disclosed in the '485 publication, the device 100 is part of a computer system that can include a video frame grabber card and associated software, memory storage, a display screen, a user input device (keyboard or touch pad, etc.), image processing software and a counter. Associated with the personal computer is the printer which prints gemstone certificates. In addition, the personal computer includes communication software that permits the computer to communicate over a network with other devices, such as a wired or wireless connection.

The following detailed description is directed to systems and methods for gemstone registration by generating an optical fingerprint of the gemstone and for capturing one or more image using the secondary camera. The referenced systems and methods are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods. Accordingly, aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather are to provide an understandable description of the systems and methods.

It will be understood that reference characters listed below and Figures mentioned below are set forth in the '485 publication of which reference is made.

An exemplary computer system is shown as a block diagram in FIG. 13 which is a high-level diagram illustrating an exemplary configuration of a gemstone registration system 10 that utilizes and controls the operation of device 100. In one implementation, computing device 15 can be a personal computer or server. In other implementations, computing device 15 can be a tablet computer, a laptop computer, or a mobile device/smartphone, though it should be understood that computing device 15 of gemstone registration system 10 can be practically any computing device and/or data processing apparatus capable of embodying the systems and/or methods described herein.

Computing device 15 of gemstone registration system 10 includes a processor 11 which is operatively connected to various hardware and software components that serve to enable operation of the gemstone registration system 10. The processor 11 is operatively connected to a memory 12. Processor 11 serves to execute instructions for software that can be loaded into memory 12. Processor 11 can be a number of processors, a multi-processor core, or some other type of processor, depending on the particular implementation. Further, processor 11 can be implemented using a number of heterogeneous processor systems in which a main processor is present with secondary processors on a single chip. As another illustrative example, processor 11 can be a symmetric multi-processor system containing multiple processors of the same type.

Preferably, memory 12 and/or storage 19 are accessible by processor 11, thereby enabling processor 11 to receive and execute instructions stored on memory 12 and/or on storage 19. Memory 12 can be, for example, a random access memory (RAM) or any other suitable volatile or non-volatile computer readable storage medium. In addition, memory 12 can be fixed or removable. Storage 19 can take various forms, depending on the particular implementation. For example, storage 19 can contain one or more components or devices such as a hard drive, a flash memory, a rewritable optical disk, a rewritable magnetic tape, or some combination of the above. Storage 19 also can be fixed or removable.

One or more software modules 13 are encoded in storage 190 and/or in memory 12. The software modules 13 can comprise one or more software programs or applications having computer program code or a set of instructions executed in processor 11. Such computer program code or instructions for carrying out operations for aspects of the systems and methods disclosed herein can be written in any combination of one or more programming languages, including an object oriented programming language such as Java, Smalltalk, C++, Python, and JavaScript or the like and conventional procedural programming languages, such as the "C" programming language or similar programming languages. The program code can execute entirely on computing device 15, partly on computing device 15, as a stand-alone software package, partly on computing device 15 and partly on a remote computer/device, or entirely on the remote computer/device or server. In the latter scenario, the remote computer can be connected to computing device 15 through any type of network, including a local area network (LAN) or a wide area network (WAN), or the connection can be made to an external computer (for example, through the Internet 16 using an Internet Service Provider).

One or more software modules 13, including program code/instructions, are located in a functional form on one or more computer readable storage devices (such as memory 12 and/or storage 19) that can be selectively removable. The software modules 13 can be loaded onto or transferred to computing device 15 for execution by processor 11. It can also be said that the program code of software modules 13 and one or more computer readable storage devices (such as memory 12 and/or storage 19) form a computer program product that can be manufactured and/or distributed in accordance with the present invention, as is known to those of ordinary skill in the art.

It should be understood that in some illustrative embodiments, one or more of software modules 13 can be downloaded over a network to storage 19 from another device or system via communication interface 15 for use within gemstone registration system 10. For instance, program code stored in a computer readable storage device in a server can be downloaded over a network from the server to gemstone registration system 10.

Preferably, included among the software modules 13 is a gemstone alignment module 61, an imaging module 62, an analysis module 63, and a user interface module 65 that are executed by processor 11. Execution of the software modules 13 configures the processor 11 to perform various operations relating to gemstone alignment and imaging and analysis with computing device 15, as will be described in greater detail below. It should be understood that while software modules 13 can be embodied in any number of computer executable formats, in certain implementations one or more of the software modules 13 comprise one or more applications that are configured to be executed at computing device 15 in conjunction with one or more applications or 'apps' executing at remote devices, such as computing device(s) 30, 32, and/or 34 and/or one or more viewers such as internet browsers and/or proprietary applications. Furthermore, in certain implementations, software modules 13 can be configured to execute at the request or selection of a user of one of computing devices 30, 32, and/or 34 (or any other such user having the ability to execute a program in relation to computing device 15, such as a network administrator), while in other implementations computing device 15 can be configured to automatically execute software modules 13 without requiring an affirmative request to execute. It should also be noted that while FIG. 13 depicts memory 12 oriented locally on the computing device 15, in an alternate arrangement, memory 12 can be operatively connected to the processor 11 of computing device 15. In addition, it should be noted that other information and/or data relevant to the operation of the present systems and methods (such as database 18) can also be stored on storage 19, as will be discussed in greater detail below.

Also preferably stored on storage 19 is database 18. As will be described in greater detail below, database 18 contains and/or maintains various data items and elements that are utilized throughout the various operations of gemstone registration system 10, including but not limited to gemstone identification information 40, images 42, etc., as will be described in greater detail herein. It should be noted that although database 18 is depicted as being configured locally to computing device 15, in certain implementations database 18 and/or various of the data elements stored therein can be located remotely (such as on a remote device or server—not shown) and connected to computing device 15 through network 16, in a manner known to those of ordinary skill in the art. Since device 100 includes both a primary and secondary camera image information and data from each camera can be stored in memory or the like.

A user input device 14 is also operatively connected to the processor 11. The interface can be one or more input device(s) such as switch(es), button(s), key(s), a touch screen, etc. Interface serves to facilitate the capture of certain information, such as operation commands, from the user as discussed in greater detail below. Interface also serves to facilitate the capture of commands from the user related to operation of the gemstone registration system 10.

An external display 90 can be operatively connected to the processor 11. Display includes a screen or any other such presentation device that enables the user to view various options, parameters, and results. By way of example, display 90 can be a digital display such as a dot matrix display or other 2-dimensional display. Display 90 can thus optionally be used in combination with the display 101 that is an integral part of the device 100.

By way of further example, user input device 14 and display 90 can be integrated into a touch screen display, such as display 101. Accordingly, the screen is used to show a graphical user interface, which can display various data and provide "forms" that include fields that allow for the entry of information by the user. Touching the touch screen at locations corresponding to the display of a graphical user interface allows the person to interact with the device to enter data, change settings, control functions, etc. So, when the touch screen is touched, the user input device communicates this change to processor, and settings can be changed, commands can be executed or user entered information can be captured and stored in the memory.

Communication interface 50 is also operatively connected to the processor 11. Communication interface 50 can be any interface that enables communication between the computing device 15 and external devices, machines and/or elements. Preferably, communication interface 50 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting computing device 15 to other computing devices and/or communication networks such as private networks and the Internet. Such connections can include a wired connection or a wireless connection (e.g. using the 802.11 standard) though it should be understood that communication interface 50 can be practically any interface that enables communication to/from the processor 11 of the computing device 15.

In the description that follows, certain embodiments and/or arrangements are described with reference to acts and symbolic representations of operations that are performed by one or more devices, such as the gemstone registration system 10 of FIG. 13. As such, it will be understood that such acts and operations, which are at times referred to as being computer-executed or computer-implemented, include the manipulation by processor 11 of electrical signals representing data in a structured form. This manipulation transforms the data and/or maintains them at locations in the memory system of the computer (such as memory 12 and/or storage 19), which reconfigures and/or otherwise alters the operation of the system in a manner understood by those skilled in the art. The data structures in which data are maintained are physical locations of the memory that have particular properties defined by the format of the data. However, while an embodiment is being described in the foregoing context, it is not meant to provide architectural limitations to the manner in which different embodiments can be implemented. The different illustrative embodiments can be implemented in a system including components in addition to or in place of those illustrated for the gemstone registration system 10. Other components shown in FIG. 13 can be varied from the illustrative examples shown. The different embodiments can be implemented using any hardware device or system capable of running program code. In another illustrative example, gemstone registration system 10 can take the form of a hardware unit that has circuits that are manufactured or configured for a particular use. This type of hardware can perform operations without needing program code to be loaded into a memory from a computer readable storage device to be configured to perform the operations.

For example, computing device 15 can take the form of a circuit system, an application specific integrated circuit (ASIC), a programmable logic device, or some other suitable type of hardware configured to perform a number of operations. With a programmable logic device, the device is configured to perform the number of operations. The device can be reconfigured at a later time or can be permanently configured to perform the number of operations. Examples of programmable logic devices include, for example, a programmable logic array, programmable array logic, a field programmable logic array, a field programmable gate array, and other suitable hardware devices. With this type of implementation, software modules 13 can be omitted because the processes for the different embodiments are implemented in a hardware unit.

In still another illustrative example, computing device 15 can be implemented using a combination of processors found in computers and hardware units. Processor 11 can have a number of hardware units and a number of processors that are configured to execute software modules 13. In this example, some of the processors can be implemented in the number of hardware units, while other processors can be implemented in the number of processors.

In another example, a bus system can be implemented and can be comprised of one or more buses, such as a system bus or an input/output bus. Of course, the bus system can be implemented using any suitable type of architecture that provides for a transfer of data between different components or devices attached to the bus system. Additionally, communications interface 50 can include one or more devices used to transmit and receive data, such as a modem or a network adapter.

Embodiments and/or arrangements can be described in a general context of computer-executable instructions, such as program modules, being executed by a computer. Generally, program modules include routines, programs, objects, components, data structures, etc., that perform particular tasks or implement particular abstract data types.

It should be further understood that while the various computing devices and machines referenced herein, including but not limited to computing device 15, computing devices 30, 32, and 34 are referred to herein as individual/single devices and/or machines, in certain implementations the referenced devices and machines, and their associated and/or accompanying operations, features, and/or functionalities can be arranged or otherwise employed across any number of devices and/or machines, such as over a network connection, as is known to those of skill in the art.

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present invention need not reside on a single computer or processor, but can be distributed in a modular fashion amongst a number of different computers or processors to implement various aspects of the systems and methods disclosed herein.

Thus, illustrative embodiments and arrangements of the present systems and methods provide a computer implemented method, computer system, and computer program product for determining product arrangements. The block diagram in the figures illustrates the architecture, functionality, and operation of possible implementations of systems, methods and computer program products according to various embodiments and arrangements. In this regard, each block in the block diagram can represent a module, segment, or portion of code, which comprises one or more executable instructions for implementing the specified logical function (s). It should also be noted that, in some alternative implementations, the functions noted in the block may occur out of the order noted in the figure. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Device 100 can thus be connected to the computer system 10 using conventional means including being both wired (use of a cable) and wireless means. Data generated and recorded by the device 100 can thus be transferred to the computing device 15 that executes software (application 17).

The user interface of the present device can be similar to those described in the '485 publication.

In the exemplary embodiment, the processor configured by executing one or more of the software modules 13 including, preferably, user interface module 65, displays a section of the display screen that represents a user interface section that allows the user to easily move the gimbal assembly 300 so as to make adjustments to the position of the gemstone and properly position the gemstone into registration (axial alignment) with the light beam. This is a manual mode in that the alignment is done based on commands generated by the user, for example, by the user clicking different regions of the user interface section (alignment pad) using the user input device 14. For example, the user interface section can be a rectangular box that shows the centered position of the light beam and shows a mark or other indicia that represents the gemstone's position on the plate. As discussed in applicant's other patents, the optimal alignment and the centered position of the gemstone results when the mark representing the gemstone's position is axially aligned with (in registration) with the light beam. A user interface indicator (such as a cursor that moves in response to movement of user input device 14 e.g., a mouse or the like) is moved along the user interface section 12 of display 90 to cause a signal to be delivered by the processor 11 to the motors that the control the gimbal assembly and the motion plate according to the user interaction with the user input device 14. This action is thus a move and click motion in which the user can make the necessary adjustments to the position of the gemstone by moving and clicking a location on the user interface section which in turn causes the processor to send a control signal to one or more of the motors for causing movements of the gimbals that result in the gemstone's center being aligned. In other embodiments, the user interface section 12 can be a touch screen and the user can use a stylet or the like to select a position.

The gimbal assembly 300 is thus programmed to respond to the control signals generated by the processor which is configured by executing one or more of the software modules, including, preferably, the user interface module 65 and the gemstone alignment module 61, when the user moves the tool within the user interface section 12 and in particular, the precise control of one or more of the servo motors that control the inner and outer gimbals depends upon the current position of the gimbals and the location that is highlighted (clicked) in the user interface section 12. For example, only operation of the one of the servo motors may be needed to cause the proper adjustment of the gimbals which in turn provides adjustment of the gemstone's position. Alternatively, operation of both motors may be needed.

Thus, when the tool (e.g., cursor controlled by a mouse) is moved within the section 12 and then the user clicks on a specific location, the configured processor compares the present location of the gimbals compared to the newly selected position and then sends controls to the servo motors to cause the necessary movement of the gimbals to position the gemstone in the newly selected position by means of movement of the gimbals, which corresponds to movement of the gemstone that is supported on the transparent support the position of which is controlled by the gimbals.

It will be appreciated that the processor configured by executing one or more software modules including, preferably, user interface module 65 and imaging module 62 and analysis module 64, will cause the processor to detect the position of the gemstone and update the information shown on the display 90, 101 such that the user will readily see, in real time, the updated position of the gemstone relative to the light beam by watching the user interface section 12 and observing movement of the mark (representing the gemstone's position) relative to the light beam. The gimbals are moved until optimal registration is realized between gemstone and light beam.

The configured processor 11 thus allows proper identification of the owner of the gemstone, followed by details of the gemstone as assessed by a jeweler. Details of the gemstone include the cut, clarity, color and other characteristics. This information is keyed in using the user input 14 (e.g., a keyboard) and is stored in the database 18. In addition, the processor configured by executing one or more software modules including, preferably, the imaging module 62 causes the processor to receive the video signal from the primary camera 375 and the secondary camera and be displayed on the display screen 90 (the reflectance pattern is thus shown in real time). The camera is actually in an enclosure, as the display of the optical response from the gemstone is dependent upon ambient conditions, such as light conditions. The jeweler conducting the gemstone identification reviews the optical response captured by the camera 375 and the secondary camera and displayed on the display screen and if he determines that the gemstone requires additional power for increased clarity, he adjusts a virtual exposure control slide displayed on the computer screen using user input 14. Adjustment of this control varies the power of the diode laser. This type of laser is easily adjustable to a host of power settings and allows the jeweler a further variable for controlling the quality of the final optical response. Too much light causes "blooming" in the image or video capture of the optical response and therefore less accuracy. Not enough power results in loss of low level responses from the gemstone. It is generally preferred to adjust towards a low level while maintaining the number of "hot points" in the optical response.

The primary camera 375 and the personal computer 15 allow a jeweler to examine the video image of a properly located gemstone and adjusts the power of the laser by using the exposure control slide displayed on the computer screen. The jeweler thus adjusts the power of the laser to a level for optimum image capture. The video or initial image can use a 256 level gray scale and changes in exposure are immediately reflected in the displayed image. The 256 gray scale provides very good accuracy in distinguishing between areas which are reflected or refracted light beams and areas which do not have any significant light response.

Once the jeweler has adjusted the device and is satisfied that the video image would be suitable for recording, he actuates the virtual "CAPTURE" button displayed on display 90 which is received by the processor 11. Receiving the CAPTURE input by the processor 11, which is configured by executing one or more of the software modules 13 including, preferably, the imaging module 62, causes the primary camera 375 to capture one or more static images of the gemstone and execute image processing algorithms implementing various corrections to the image and convert the images to a monochromatic display format. In this case, the "hot spots" are now shown as black areas and the remaining area is white. As shown on the display screen of FIG. 13 of the '485 publication, there is a number of function buttons, namely "OK", "CANCELLED", and "CAPTURED", as well as an "EXPOSURE LEVEL" slide. This image has also undergone a number of corrections, one of which is for the angle at which the camera is located relative to the gemstone. In addition, the configured processor processes the images to make certain corrections to compensate for characteristics of the LEDs and factors introduced by the particular camera. These corrections are determined upon start-up of the camera. For example, the LEDs produce hot spots in the image captured by the camera, but serve the useful purpose of locating the center of the image. Accordingly, during start-up, a background image is captured which includes the effect of these LEDs and other characteristics of the particular camera and is stored in memory or storage. These effects can then be removed by the image processing steps to leave a captured image more accurately reflecting the characteristics of the gemstone. It should be understood that the captured image reflecting the characteristics of the gemstone can also be referred to as the gemprint. It will be appreciated that the above features are merely exemplary and are not required in all applications.

Once the user presses the CAPTURE button, the static captured image is displayed at area of the display screen and the static captured image is stored in memory or storage and serves as the fingerprint for the gemstone.

With the images shown in FIG. 13 of the '485 publication, the jeweler then has the option to confirm that the image is appropriate for recordal and if this is the case, one would execute the CAPTURE button. This image is then combined with the inputted information regarding the identity of the owner and the various characteristics of the gemstone for recordal purposes and is stored in storage 19 (e.g., database 18). It is also possible at that time to provide a certificate of this optical display, the identity of the owner and gemstone characteristics.

Other features that can be part of the present device and the operation of the present device can be understood by a review of Applicant's previous patents that are incorporated herein.

As discussed hereinbefore, the user can control operation of the secondary camera through the user interface described herein.

The present system can be used by the jeweler in a number of different ways. The most simplified and common service provided by the jeweler is with respect to gemstone identification and recordal. In this case, the owner of the gemstone wishes to have the gemstone properly identified by its optical image as well as the physical characteristics of the stone and have this combined information recorded in a centralized database. In this way, the user knows that his stone has been accurately "fingerprinted" and this record is maintained in a central database for future retrieval. If the gemstone is stolen, the optical image may be transferred to a database of stolen gemstones and any recovered gemstones can be cross-checked against this database. One of the major problems is matching recovered stolen gemstones with their owner. This problem is overcome by the above arrangement where the stolen gemstone database is searchable by the police.

A further service provided by the jeweler allows verification of gemstones and can be used by the jeweler with respect to jewelry repair.

It will be understood that the device 100 of the present invention can perform any of the operations described in the '485 publication and/or have any of the features described in the '485 publication. The device 100 can thus perform any of the imaging analysis described in the '485 publication and the device 100 can be used as a gemstone simulant detector as described in detail in the '485 publication. Further, the device 100 can have any of the light performance functionality described in the '485 publication. Thus, the gemstone registration device 100 can also inform an individual about how well the gemstone is cut, by looking at a plurality (e.g., four or more) different metrics of light performance, or light handling ability. As set forth below, the different metrics can include but are not limited to light return, optical symmetry, scintillation, and optionally, light dispersion and brilliance of any given gemstone.

The gemstone registration device 100 can thus offer direct light assessment functionality to supplement the gemprint identification information that can be supplied to a person, such as a manufacturer, a retailer, a consumer, etc. In terms of the device itself, FIG. 1 shows one exemplary gemstone registration device 100 that includes the additional functionality described herein. It should be understood that the gemstone registration device 100 can include a computing device, such as computing device 15, for controlling the operation of the gemstone registration device 100 in accordance with the disclosed embodiments.

In addition to the properties described in the '485 publication, the device 100 is configured to perform optical brilliance analysis.

The device directly assesses the overall return of light to the viewer, called 'brilliance'.

The Optical Brilliance image is actually a digital photograph of the diamond taken in a special lighting environment that creates a strong contrast between the bright and dark areas. The image is then processed in a proprietary computer program that calculates the percentage of brilliance and the amount of light loss. This is a scientifically accurate and repeatable way to measure brilliance. The light gray areas of the image are facet outlines resulting from image processing to provide a realistic representation of the diamond's unique faceting.

In the Optical Brilliance Analysis image on a sample certificate, the white represents the light return and the blue represents areas of light loss. The light return is quantified based on measurable light return (aka—performance) and then graded as: Excellent, Very Good, Good, Fair or Poor.

Since the Optical Brilliance is measured by direct assessment, meaning that it is judged based on the way each diamond actually performs rather than a theoretical model, the brilliance image of each individual diamond will always look slightly different.

A user can explain to your customer that brilliance is what gives a diamond its life, and what makes a diamond shine from across a room. Diamonds with a low percentage of brilliance look dull and dark. You can demonstrate to your customer how their diamond compares to other grades by showing them the scale on the cover panel of the certificate.

While the invention has been described in connection with certain embodiments thereof, the invention is capable of being practiced in other forms and using other materials and structures. Accordingly, the invention is defined by the recitations in the claims appended hereto and equivalents thereof.

What is claimed is:

1. A device for measuring light performance of a gemstone in an automated manner comprising:
   a platform for receiving the gemstone;
   a light source for directing a focused beam of light onto the gemstone to produce an output of the internal refraction and reflection characteristics of the gemstone including reflected light beams having particular locations, sizes and intensities;
   an automated positioning mechanism for changing a position of the gemstone relative to the focused beam of light, wherein the automated positioning mechanism is configured to change a yaw motion of the platform on which the gemstone rests by causing controlled rotation of the platform;
   a first imaging device for recording the output in a manner to record the relative size and location of the reflected light beams; and
   wherein the device is configured to analyze the light performance of the gemstone.

2. The device of claim 1, wherein the automated positioning mechanism is configured to also change a pitch and roll of the platform.

3. The device of claim 2, wherein the automated positioning mechanism includes: (a) a gimbal assembly for changing a position of the gemstone relative to the focused beam of light, wherein the gimbal assembly includes a first gimbal and a second gimbal, the first gimbal pivoting about a first axis and the second gimbal pivoting about a second axis that is perpendicular to the first axis, the platform being coupled to the second gimbal such that the platform extends across a center opening of the second gimbal, the first and second gimbals being configured to change the pitch and roll of the platform; (b) a yaw frame to which the first and second gimbals are mounted, the yaw frame being free to rotate so as to change the yaw of the platform due to rotation of the first and second gimbals when the yaw frame rotates.

4. The device of claim 3, wherein the first gimbal is operatively coupled to a first motor by a first drive shaft for controllably rotating the first gimbal about the first axis and the second gimbal is operatively coupled to a second motor by a second drive shaft for controllably rotating the second gimbal about the second axis, wherein the first and second motors are fixedly attached to the yaw frame and rotate therewith.

5. The device of claim 4, wherein the first and second motors are controlled by signals generated by a processor and the device is part of a computer system that includes a display screen on which a user interface section is displayed, the user interface section having a user interface tool that can be moved along the user interface section by the user to cause the processor to generate signals that result in incremental movement of one or more of the gimbals resulting in the gemstone being repositioned relative to the light source.

6. The device of claim 3, wherein the yaw frame is coupled to a yaw gear that is intimately coupled to a powered drive gear to cause controlled rotation of the yaw frame.

7. The device of claim 6, wherein the first and second gimbals are disposed within a hollow center of the yaw frame and the yaw gear is disposed circumferentially about the first and second gimbals such that the yaw gear completely surrounds the first and second gimbals.

8. The device of claim 6, wherein the powered drive gear comprises a pinion gear that is operatively coupled to a yaw motion motor.

9. The device of claim 3, wherein the gimbal assembly and the yaw frame are coupled to a motion plate which is configured to be controllably moved in both an x-direction and a y-direction so as to allow the gemstone to be moved in the x-direction and the y-direction.

10. The device of claim 9, further including a plurality of 2-way slide supports that are free to move along a first pair of guide rails in the x-direction resulting in the motion plate moving in the x-direction and a plurality of second guide rails that are coupled to the 2-way slide supports and a plurality of 1-way slide supports to which the motion plate is mounted, the 1-way slide supports being free to move along the pair of second guide rails resulting in the motion plate moving in the y-direction.

11. The device of claim 10, wherein the pair of first guide rails are parallel to one another and the pair of second guide rails are parallel to one another and are disposed perpendicular to the first guide rails, each 2-way slide support having a first bore formed therein for receiving one end of one first guide rail and a second bore formed therein for receiving one end of one second guide rail, the first and second bores lying in different planes and being formed orthogonal to one another.

12. The device of claim 9, wherein a first motor controls the movement of the motion plate in the x-direction and a separate second motor controls the movement of the motion plate in the y-direction.

13. The device of claim 1, wherein the platform is coupled to a yaw assembly that includes a yaw frame to which the platform is coupled and a yaw gear that is separate from and mounted to the yaw frame and is operatively connected to a motor by a drive gear to allow the yaw frame to be controllably rotated and thereby rotate the platform, wherein the yaw gear completely surrounds the platform.

14. The device of claim 13, wherein the yaw gear comprises an annular shaped gear with the platform being centrally located within a center opening of the annular shaped gear.

15. The device of claim 14, wherein the yaw gear includes teeth formed 360° about an outer peripheral edge thereof.

16. The device of claim 1, wherein the platform has a planar top surface to allow the gemstone to be oriented with its table facing down and seated against the planar top surface of the platform, the platform being formed of a material that allows the focused beam of light to pass therethrough and contact the gemstone disposed on the planar top surface.

17. The device of claim 1, further including:
an integral display that is mounted within a housing of the device and moves between a stored position in which the display is contained within the housing and a deployed position in which the display is disposed external to the housing, the display for graphically displaying: at least one captured first image that represents a total light return for the gemstone and a respective light return grade for the gemstone and at least one captured second image that represents the optical symmetry of the gemstone and a respective optical symmetry grade for the gemstone.

18. The device of claim 1, wherein the first imaging device comprises a primary camera.

19. The device of claim 1, further including a secondary imaging device for capturing an image of the gemstone.

20. The device of claim 1, wherein the device is configured to perform an optical brilliance analysis.

21. The device of claim 1, wherein the platform is rotated about an axis that is parallel to a longitudinal axis of the light beam.

22. A device for measuring light performance of a gemstone in an automated manner comprising:
a platform for receiving the gemstone;
a light source for directing a focused beam of light onto the gemstone to produce an output of the internal refraction and reflection characteristics of the gemstone including reflected light beams having particular locations, sizes and intensities;
an automated positioning mechanism for changing a position of the gemstone relative to the focused beam of light, wherein the automated positioning mechanism is configured to change a yaw motion of the platform on which the gemstone rests;
a first imaging device for recording the output in a manner to record the relative size and location of the reflected light beams;
a secondary imaging device for capturing an image of the gemstone; and
wherein the device is configured to analyze the light performance of the gemstone and the secondary imaging device comprises a secondary camera that moves between a home position in which it is spaced from the light source and an operating position in which the secondary camera is disposed below the gemstone and the light source is not actuated.

23. The device of claim 22, further including a light system for illuminating the gemstone, wherein the light system and the secondary imaging device are positioned such that, in the operating position, the secondary imaging device captures an image of the gemstone that is illuminated by the light system.

24. The device of claim 23, wherein the light system includes a first light system disposed below the platform for illuminating the gemstone from an underside and a second light system disposed above the platform for illuminating the gemstone from above the platform.

25. The device of claim 24, wherein one or more of the first and second light systems are:
a) Energy efficient LED's;
b) long wave and shortwave UV lights; or
c) white lights—added to a stage of the secondary camera for direct assessment of scintillation and dispersion measurements.

26. The device of claim 22, wherein the secondary camera is configured to perform one or more of the following operations:
a) photography—the secondary camera takes an image of the gemstone or gemstone jewelry placed on the platform and provides an additional point of identification;
b) inclusion photography—a user can manipulate the gemstone in all directions, planes, and angles, to direct the secondary camera in an optimal position to capture any inclusions contained in the gemstone;
c) shape detection—the secondary camera takes a photograph of the gemstone, and using many parameters, including edge detection, the device is able to determine the shape of the gemstone;
d) measurements—Adding to the shape detection, the photograph will allow us to measure the length and width or minimum and maximum diameter of the stone;
e) weight estimation—in combination with the shape detection, and measurement analysis, and average depth % for individual shapes, the device is able to approximate the weight of the gemstone;
f) damage detection—photographing the gemstone using the secondary camera will allow for damage, chips, nicks, scratches, etc. to be identified and included as points of identification;
g) ultraviolet characteristics—the device is able to capture, photograph, and measure the gemstones reaction to the longwave and shortwave UV lights to provide further points of identification; and
h) light return/optical symmetry, scintillation, dispersion—the device is able to capture both the output of the laser/white light reflections, but also, the direct assessment image of the gemstone when exposed to varying light conditions, backgrounds, and electro-optical settings.

27. A device for measuring light performance of a gemstone in an automated manner comprising:
a platform for receiving the gemstone;
a light source for directing a focused beam of light onto the gemstone to produce an output of the internal refraction and reflection characteristics of the gemstone including reflected light beams having particular locations, sizes and intensities;
an automated positioning mechanism for changing a position of the gemstone relative to the focused beam of light, wherein the automated positioning mechanism is configured to change a yaw motion of the platform on which the gemstone rests;
a first imaging device for recording the output in a manner to record the relative size and location of the reflected light beams; and
wherein the device is configured to analyze the light performance of the gemstone; wherein the device includes a housing with a cover that moves between an open and closed position, the cover being positioned over the platform to allow access to the platform when the cover is in the open position, wherein an underside of the cover includes a concave shape dome structure that seats against a recessed base plate located above the platform, the base plate including a center opening through which the platform is accessed and the concave shaped dome covers the center opening in the closed position.

28. The device of claim 27, wherein a light source is provided in the base plate, the light source comprising a plurality of lights that are positioned such that the lights are below the concave shaped dome when the cover is in the closed position.

29. The device of claim 28, wherein the plurality of lights comprises LEDs.

30. A device for measuring light performance of a gemstone in an automated manner comprising:
a platform for receiving the gemstone;
a light source for directing a focused beam of light onto the gemstone to produce an output of the internal refraction and reflection characteristics of the gemstone including reflected light beams having particular locations, sizes and intensities;
an automated positioning mechanism for changing a position of the gemstone relative to the focused beam of light, wherein the automated positioning mechanism includes: (a) a gimbal assembly for changing a position of the gemstone relative to the focused beam of light, the gimbal assembly including a first gimbal that is operatively coupled to a first motor and a second gimbal that is operatively coupled to a second motor and (b) a yaw frame to which the first and second gimbals are mounted, the yaw frame being free to rotate so as to move the platform in a yaw motion due to rotation of the first and second gimbals when the yaw frame rotates, wherein the first and second motors are attached to and carried by the yaw frame;
a first imaging device for recording the output in a manner to record the relative size and location of the reflected light beams; and
wherein the device is configured to analyze the light performance of the gemstone.

31. The device of claim 30, wherein the change in yaw motion results in the platform being rotated about an axis that is parallel to a longitudinal axis of the light beam.

32. The device of claim 30, further including a yaw gear to which the yaw frame is attached, the yaw gear being operatively coupled to a driven gear such that rotation of the driven gear is translated into rotation of the yaw gear, the yaw gear comprising an annular shaped gear with the platform being centrally located within a center opening of the annular shaped gear.

33. The device of claim 32, wherein the yaw gear includes teeth formed 360° about an outer peripheral edge thereof.

34. The device of claim 32, wherein the platform and yaw gear are concentric to one another.

* * * * *